(12) United States Patent
Bolster et al.

(10) Patent No.: US 10,893,687 B2
(45) Date of Patent: Jan. 19, 2021

(54) ANIMAL FEED COMPOSITION

(71) Applicant: P. Guinane Pty. Ltd., Kingscliff (AU)

(72) Inventors: Paul Bolster, Chinderah (AU); Patricia Bolster, Chinderah (AU)

(73) Assignee: P. Guinane Pty. Ltd., Kingscliff (AU)

( * ) Notice: Subject to any disclaimer, the term of this patent is extended or adjusted under 35 U.S.C. 154(b) by 571 days.

(21) Appl. No.: 15/863,958

(22) Filed: Jan. 7, 2018

(65) Prior Publication Data

US 2018/0279649 A1 Oct. 4, 2018

Related U.S. Application Data

(63) Continuation of application No. 14/348,597, filed as application No. PCT/AU2012/001153 on Sep. 25, 2012, now abandoned.

(30) Foreign Application Priority Data

Sep. 29, 2011 (AU) .............................. 2011904005

(51) Int. Cl.
| | | |
|---|---|---|
| *A61K 36/00* | (2006.01) | |
| *A23K 20/10* | (2016.01) | |
| *A23K 20/158* | (2016.01) | |
| *A23K 50/75* | (2016.01) | |
| *A61K 36/61* | (2006.01) | |

(52) U.S. Cl.
CPC ............ *A23K 20/10* (2016.05); *A23K 20/158* (2016.05); *A23K 50/75* (2016.05); *A61K 36/61* (2013.01)

(58) Field of Classification Search
CPC ...................................................... A61K 36/00

USPC ........................................................ 424/725
See application file for complete search history.

(56) References Cited

FOREIGN PATENT DOCUMENTS

| | | |
|---|---|---|
| EP | 1053686 | 11/2000 |
| EP | 1053686 A1 | 11/2000 |
| JP | 2004099594 | 4/2004 |
| JP | 2004099594 A | 4/2004 |
| WO | 2005/120245 | 12/2005 |
| WO | WO-2005/120245 A1 | 12/2005 |
| WO | 2009/074215 | 6/2009 |
| WO | WO-2009/074215 A1 | 6/2009 |

OTHER PUBLICATIONS

Shanmugavelu et al.; "A fermentation assay to evaluate the effectiveness of antimicrobial agents on gut microflora", Journal of Microbiological Methods, vol. 67, pp. 93-101 (2006).
Andrew Matthews; "International Search Report"; Australian Patent Office; dated Nov. 9, 2012.
Yuxiang Bai et al., Comparison of encapsulation properties of major garlic oil components by hydroxypropyl 1-cyclodextrin, European Food Research and Technology, vol. 231, No. 4, Jun. 16, 2010, pp. 519-524.
Ponce Cevallos P.A. et al., Encapsulation of cinnamon and thyme essential oils components (cinnamaldehyde and thymol) in sz-cyclodextrin: effect of interactions wtih water on complex stability, vol. 99, No. 1, Jul. 1, 2010, pp. 70-75.
Koehler P. et al., Stabilisation of tea tree oil, SOFW-Journal Seifen, Oele, Fette, wachse, Verlag Fur Chemische Industrie, Augsburg, DE, vol. 125, No. 7, Jul. 1, 1999, pp. 10, 12-13.

*Primary Examiner* — Michael V Meller
(74) *Attorney, Agent, or Firm* — Winstead PC

(57) ABSTRACT

The present invention relates to a feed composition for an animal comprising tea tree oil, wherein the tea tree oil is present in an amount sufficient to reduce bacterial infection in the animal upon ingestion of the feed composition, and to methods for preparing such a composition.

10 Claims, 22 Drawing Sheets

1-7 days 1-14 days 1-21 days 1-35 days

Day 7

Day 14

Day 21

Day 35

1-7 days 1-14 days 1-21 days 1-35 days

ANIMAL FEED COMPOSITION

CROSS-REFERENCES TO RELATED APPLICATIONS

This application is a continuation of application Ser. No. 14/348,597 filed, Mar. 29, 2014, which is a national stage application of PCT/AU2012/001153, filed Sep. 25, 2012, which claims the benefit of AU Application No. 2011904005, filed Sep. 29, 2011, all of which are fully incorporated by reference as if fully set forth herein.

FIELD OF THE INVENTION

The present invention relates to a feed composition for animals, particularly poultry, including tea tree oil as a supplement that reduces bacterial infection in the animals. The present invention also relates to a method of protecting animals from bacterial infections by feeding a diet comprising tea tree oil to those animals. The present invention further relates to a method of preparing the feed composition to deliver tea tree oil to the animals.

BACKGROUND OF THE INVENTION

Antibiotics have been used as supplements in diets for poultry for many years and in many parts of the world. Microbial species, some of them potential pathogens, have developed resistance to a range of antibiotics that have been used in diets for over five decades. This resistance portends a serious challenge to the treatment of sick birds as well as humans. A range of products have been tested as alternatives to antibiotics, but to date, no single product has been identified that completely fits the role. A safe and broad spectrum anti-microbial product as an alternative to an antibiotic is desirable.

SUMMARY OF THE INVENTION

The present inventors have developed a feed composition which comprises tea tree oil as an effective antimicrobial agent. The present inventors have found that feeding compositions containing tea tree oil to animals maintains the health and growth of the animals. In particular, the animals maintained on a diet supplemented with tea tree oil demonstrated that their feed consumption, weight gain, feed conversion to energy and gut microbial profiles were maintained when compared with animals fed on a diet supplemented with a standard antibiotic, zinc bacitracin. In addition the present invention also demonstrates that a tea tree oil supplemented diet was able to protect the animals in a disease challenge trial involving *Salmonella sofia*.

Accordingly, the present invention provides a feed composition for an animal comprising tea tree oil wherein the tea tree oil is present in an amount sufficient to reduce bacterial infection in the animal upon ingestion of the feed composition.

In one embodiment the tea tree oil is present in the feed composition at an amount of between 2 milligrams and 70 milligrams per kilogram of the composition. Thus, the tea tree oil may be present in an amount of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 mg/kg of feed composition. For example, the tea tree oil may be present in an amount of 2, 3, 4, 6, 8, 12, 16, 24, 32, 35, 48, 50 or 65 mg/kg of feed composition.

In another embodiment the feed composition further comprises a carrier agent for the tea tree oil. The carrier agent may be present in an amount of from 1 ml/kg of feed composition to 50 ml/kg of feed composition. For example, the carrier agent may be present in an amount of from about 10 ml/kg to about 40 ml/kg of feed composition, or from about 15 ml/kg to about 30 ml/kg of feed composition, or may be present in an amount of about 20 ml/kg of feed composition. Preferably, the carrier agent is present in an amount of about 20 ml/kg of feed composition.

The carrier agent may be present in an amount of from 0.1% to 10% by weight of the feed composition. For example, the carrier agent may be present in an amount of from 0.5% to 5%, or from 1% to 3%, or at about 2% by weight of the feed composition. Preferably, the carrier agent is present in an amount of about 2% by weight of the feed composition.

In one embodiment the carrier agent for the tea tree oil is a vegetable oil, such as rapeseed oil or canola oil. Any carrier agent, such as any vegetable oil, and preferably, rapeseed oil or canola oil, may be present in the feed composition in any of the amounts described herein.

In one embodiment the carrier agent is canola oil. The canola oil may be present in an amount of 20 ml/kg of composition.

In one example the feed composition comprises tea tree oil and further comprises any one or more of wheat, sorghum, mung beans, tallow, canola meal, cottonseed meal, soybean meal, meat and bone meal, lysine, methionine, vitamins, trace minerals, zinc bacitracin, and any other component suitable for use in a feed composition, in any combination or permutation. For example, the feed composition may comprise any one or more of the components included in the feed composition exemplified in the Examples herein, in any combination or permutation. In addition, the feed composition may also comprise any known antibiotic other than zinc bacitracin.

In one example, the feed composition further comprises the following components at the indicated amounts (expressed as a percentage weight of the total weight of feed composition): wheat (45%), sorghum (25%), soyabean meal (12%), canola meal (8%), meat and bone meal (7%), canola oil (2%), lysine (0.3%), methionine (0.2%), vitamins, trace minerals and zinc bacitracin (0.5%).

In another embodiment, the tea tree oil may be encapsulated by an encapsulating agent. The encapsulating agent may decrease the volatility of the tea tree oil, thereby reducing loss of tea tree oil during manufacturing and/or storage of the feed composition. The encapsulating agent may be, for example, a microencapsulating agent. Suitable encapsulating agents are known in the art, and include, for example, cyclodextrins or derivatives thereof. Preferably, the encapsulating agent is a cyclodextrin. The cyclodextrin may be a α-cyclodextrin, a β-cyclodextrin, a γ-cyclodextrin or a δ-cyclodextrin. Preferably, the cyclodextrin is a β-cyclodextrin.

In one embodiment the feed composition maintains levels of feed consumption, body weight, efficiency of feed utilisation, and gut microbial profile of the animal.

The present invention also provides a method of protecting an animal from bacterial infection comprising feeding the animal with a diet comprising tea tree oil at an amount sufficient to reduce bacterial infection in the animal.

In one embodiment the method of protecting the animal comprises feeding the diet in a feeding regime comprising a starter diet and a finisher diet.

In another embodiment the method of protecting the animal comprises feeding the animal tea tree oil at an amount of between 2 milligrams and 48 milligrams per kilogram of diet.

In another embodiment the method of protecting the animal comprises feeding the animal tea tree oil at an amount of between 2 milligrams and 32 milligrams per kilogram of the starter diet.

In another embodiment the method of protecting the animal comprises feeding the animal tea tree oil at an amount of between 3 milligrams and 48 milligrams per kilogram of the finisher diet.

The present invention also provides a method of preparing a feed composition comprising the steps of
(a) combining tea tree oil with a vegetable oil, and
(b) combining (a) with a feed composition.

The method of preparing the feed composition may involve combining tea tree oil in an amount of between 2 and 50 milligrams with vegetable oil. The tea tree oil may be combined with between 20,000 and 30,000 milligrams of vegetable oil.

In one embodiment the vegetable oil is canola oil.

In another embodiment the method of preparing the feed composition comprises the step of combining tea tree oil with canola oil at least 12 hours, preferably at least 24 hours prior to the step of combining the tea tree oil/canola oil mixture with the feed composition.

Throughout this specification the word 'comprise', or variations such as 'comprises' or 'comprising', will be understood to imply the inclusion of a stated element, integer or step, or group of elements, integers or steps, but not the exclusion of any other element, integer or step, or group of elements, integers or steps.

BRIEF DESCRIPTION OF THE DRAWINGS

FIG. 1A: 1-7 days, FIG. 1B: 1-14 days, FIG. 1C: 1-21 days, FIG. 1D: 1-34 days.

FIG. 2A: day 7, FIG. 2B: day 14, FIG. 2C: day 21, FIG. 2D: day 34.

FIG. 3A: 1-7 days, FIG. 3B: 1-14 days, FIG. 3C: 1-21 days, FIG. 3D: 1-34 days.

FIG. 4A: Energy, FIG. 4B: Starch, FIG. 4C: Crude protein.

FIG. 5A: 1-7 days, FIG. 5B: 1-14 days, FIG. 5C: 1-21 days, FIG. 5D: 1-35 days.

FIG. 6A: day 7, FIG. 6B: day 14, FIG. 6C: day 21, FIG. 6D: day 35.

FIG. 7A: 1-7 days, FIG. 7B: 1-14 days, FIG. 7C: 1-21 days, FIG. 7D: 1-35 days.

FIG. 8A: Energy, FIG. 8B: Starch, FIG. 8C: Protein; *Significantly different from the ZnB group.

FIG. 9A: 1-7 days, FIG. 9B: 1-14 days, FIG. 9C: 1-21 days, FIG. 9D: 1-35 days.

FIG. 10A: day 7, FIG. 10B: day 14, FIG. 10C: day 21, FIG. 10D: day 35.

FIG. 11A: 1-7 days, FIG. 11B: 1-14 days, FIG. 11C: 1-21 days, FIG. 11D: 1-35 days.

DESCRIPTION OF THE TABLES

Figure 1A:
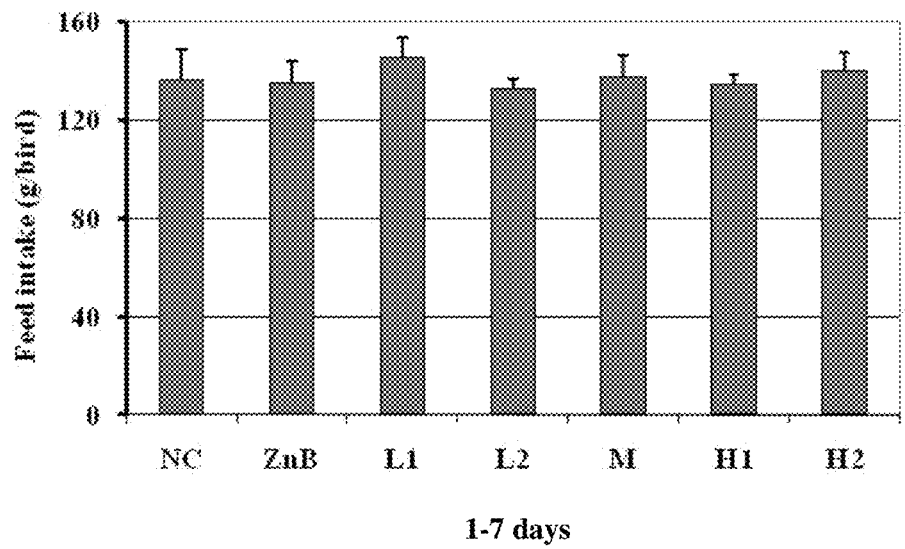
FIGS. 1A, 1B, 1C and 1D: Feed intake on diets supplemented with varying levels of tea tree oil, from hatch to different points of age.
Figure 1B:
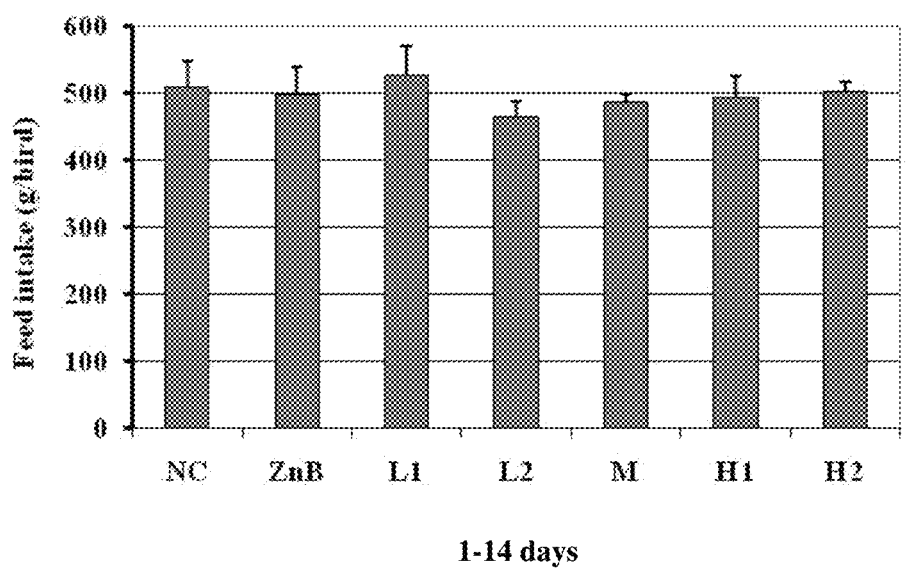
Figure 1C:
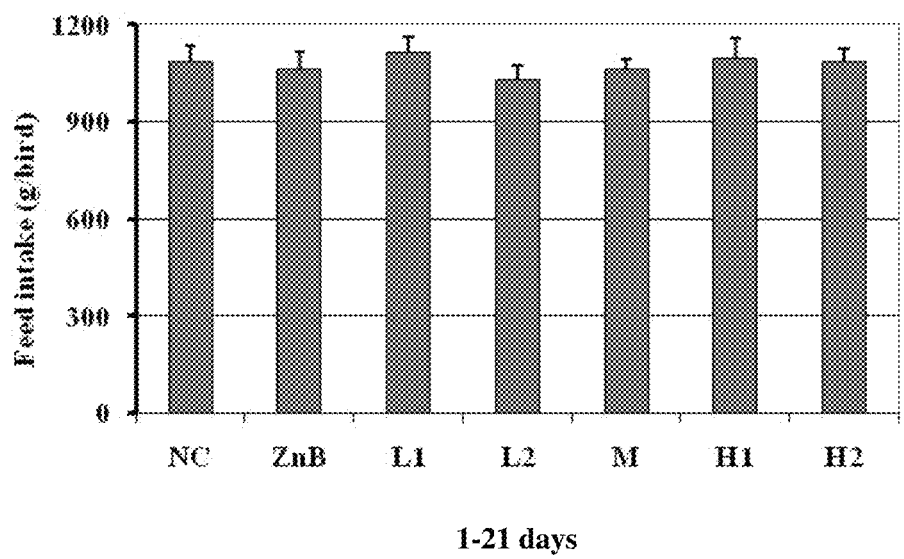
Figure 1D:
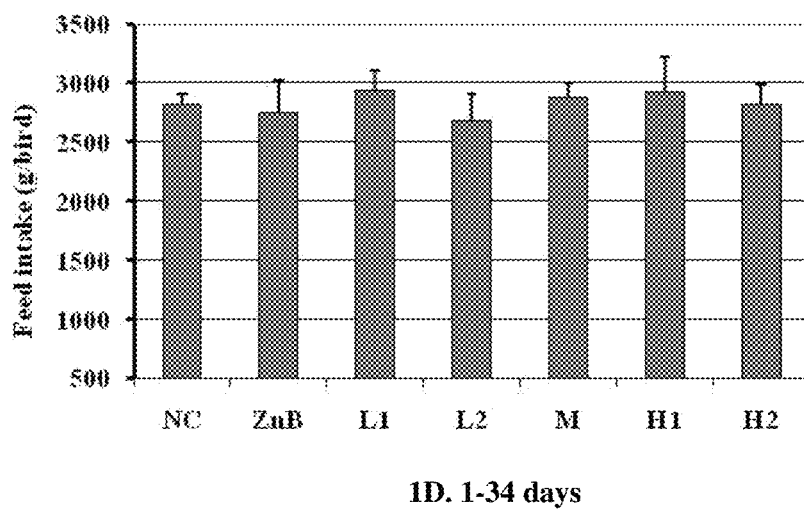
Figure 2A:
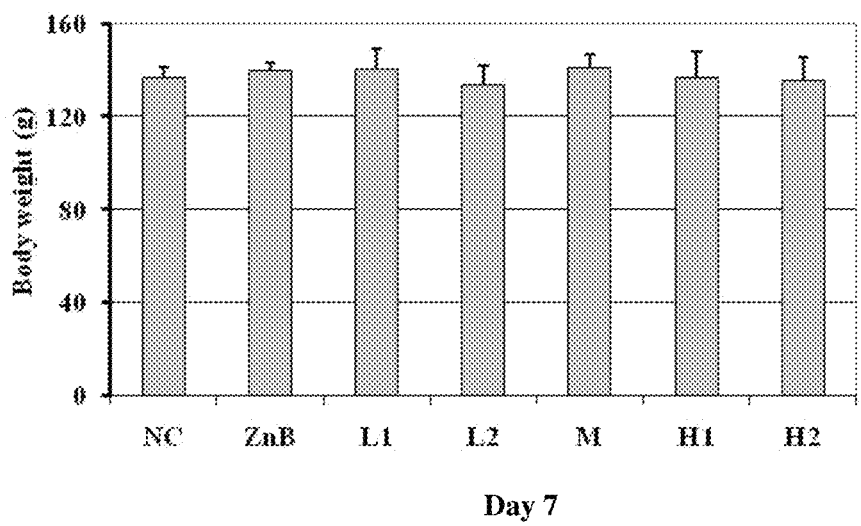
FIGS. 2A, 2B, 2C and 2D: Body weight of chicks on diets supplemented with varying levels of tea tree oil, from hatch to different points of age.
Figure 2B:
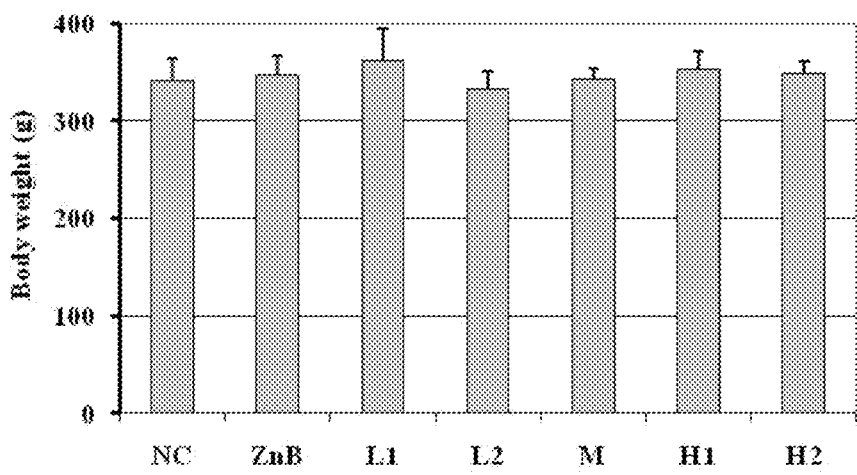
Figure 2C:
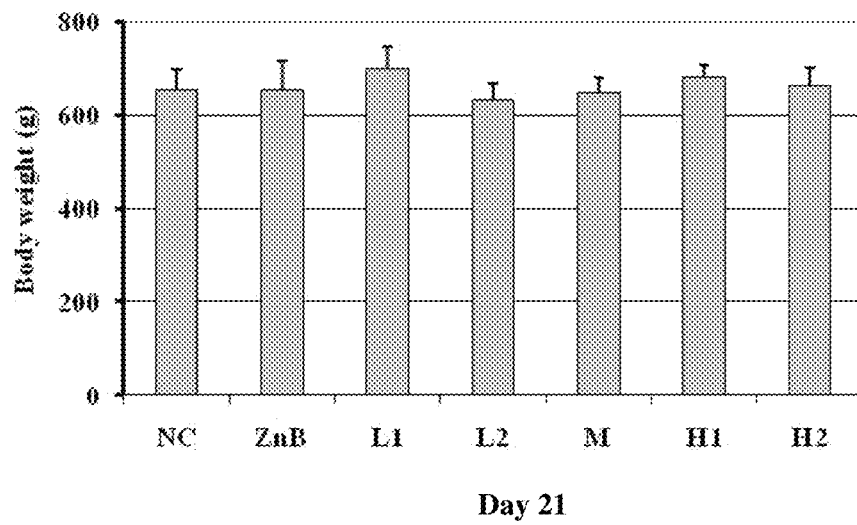
Figure 2D:
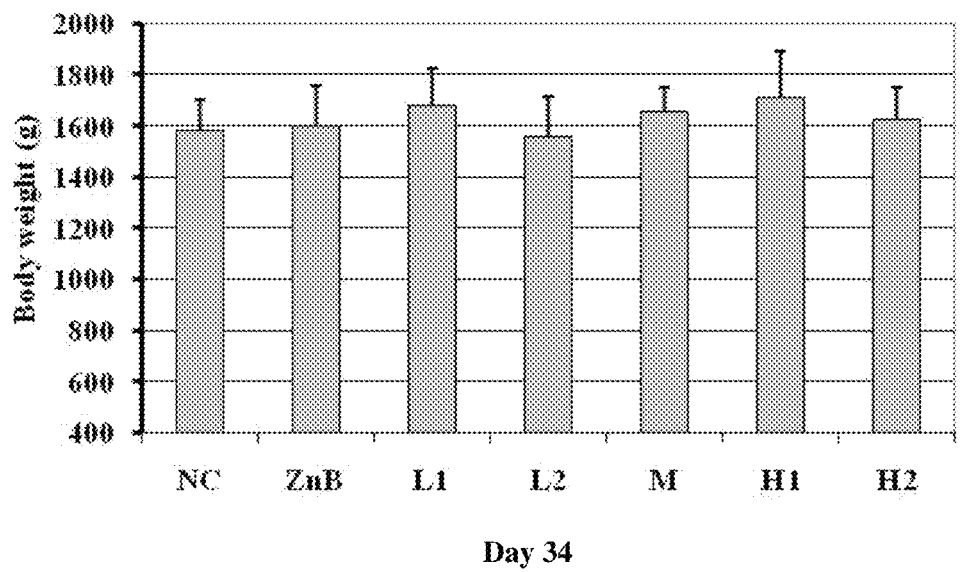
Figure 3A:
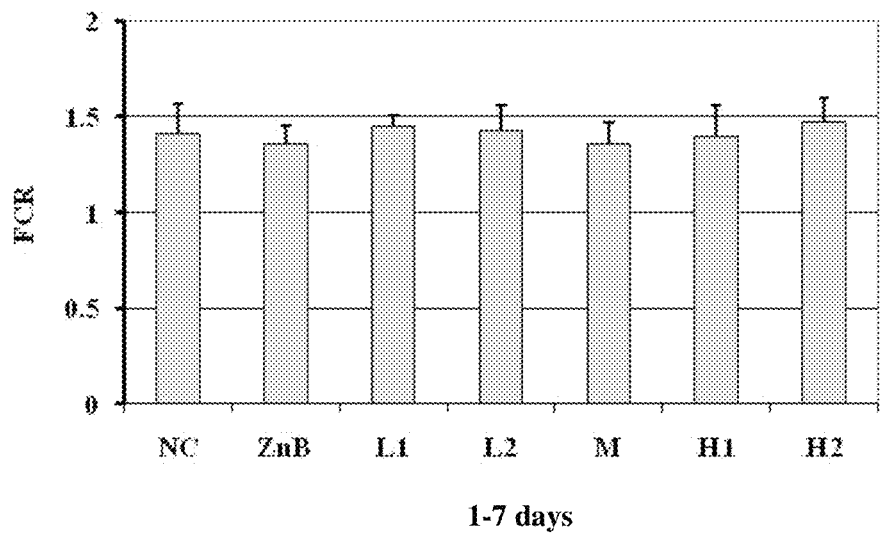
FIGS. 3A, 3B, 3C and 3D: Feed conversion ratio of chicks on diets supplemented with varying levels of tea tree oil, from hatch to different points of age.
Figure 3B:
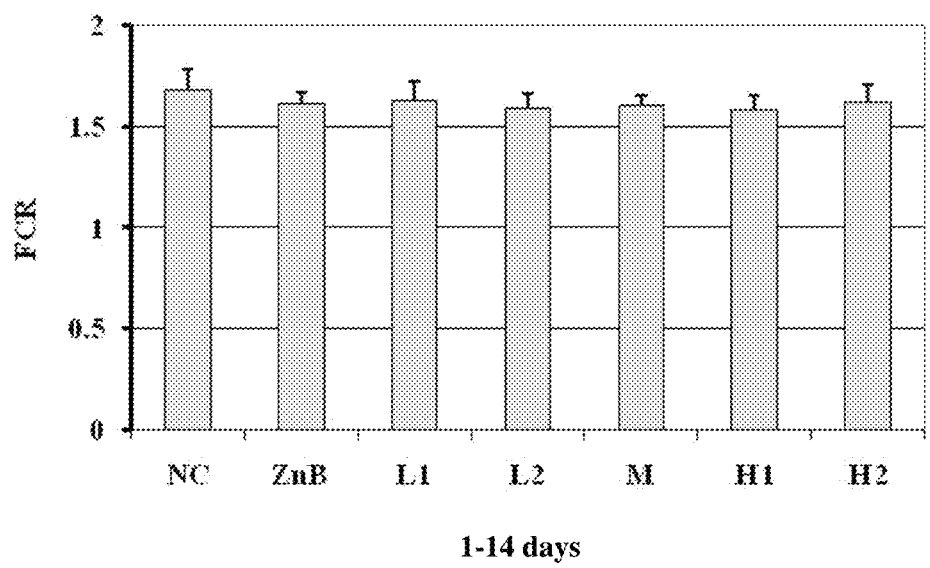
Figure 3C:
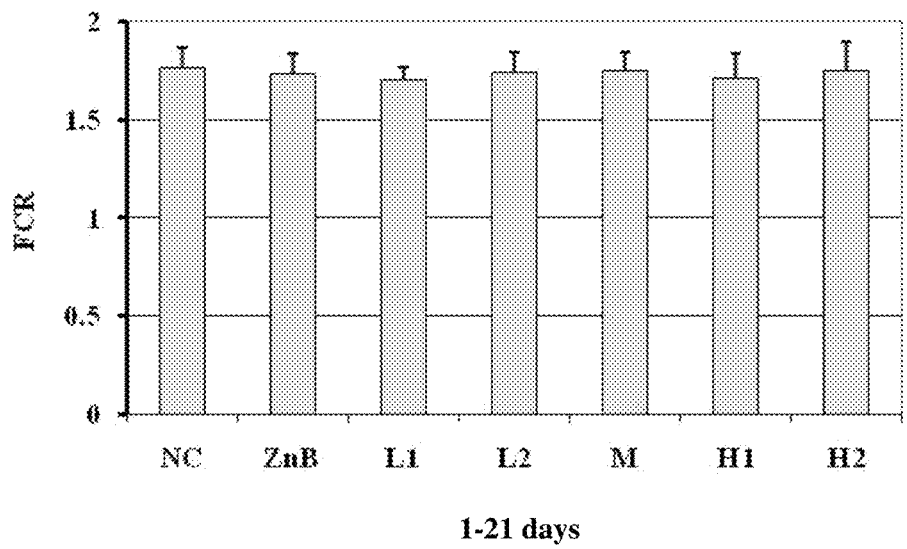
Figure 3D:
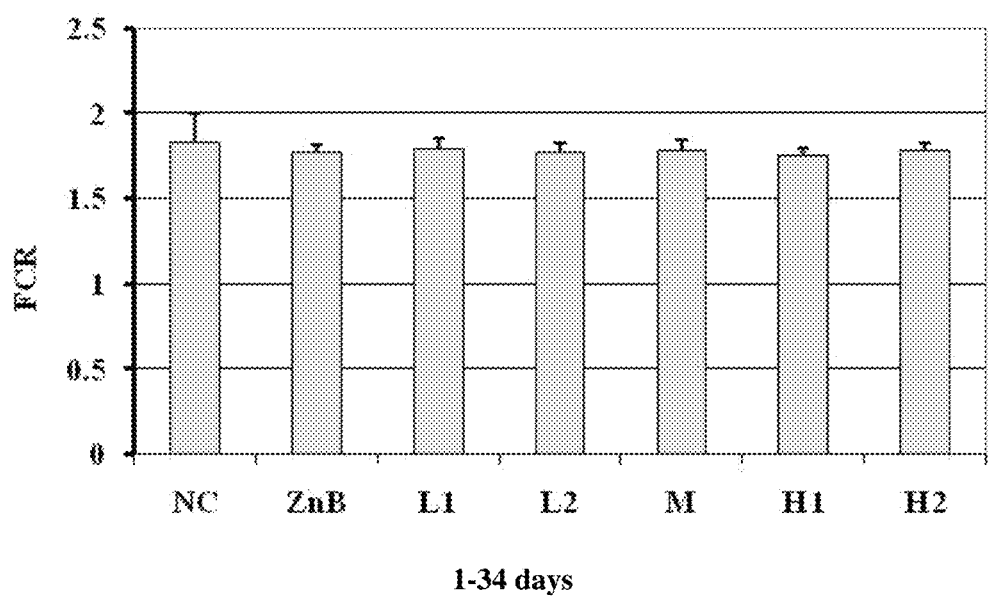
Figure 4A:
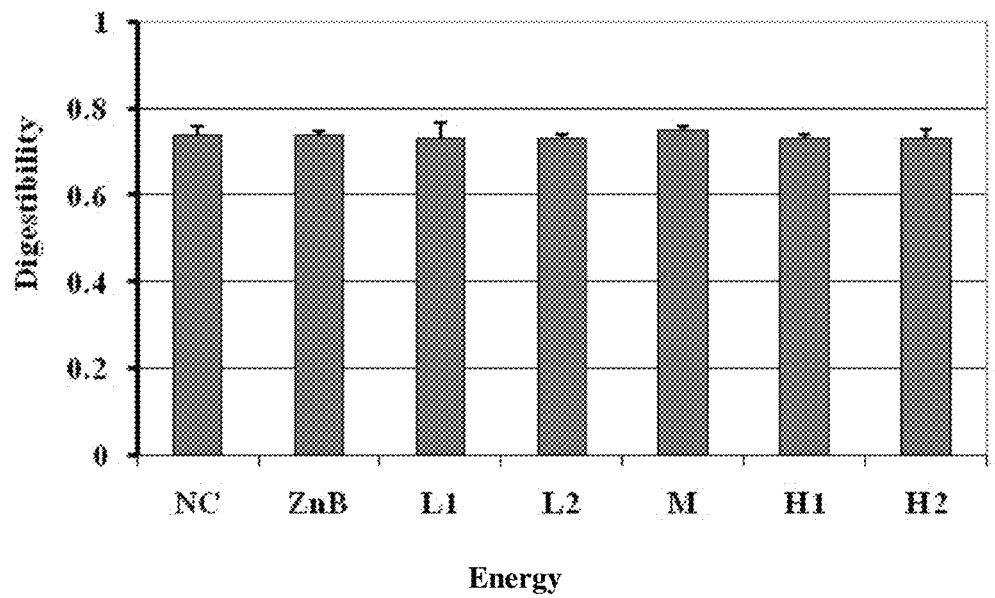
FIGS. 4A, 4B and 4C: Digestibility of dietary energy, starch and crude protein in broilers on different diets at 21 days of age.
Figure 4B:
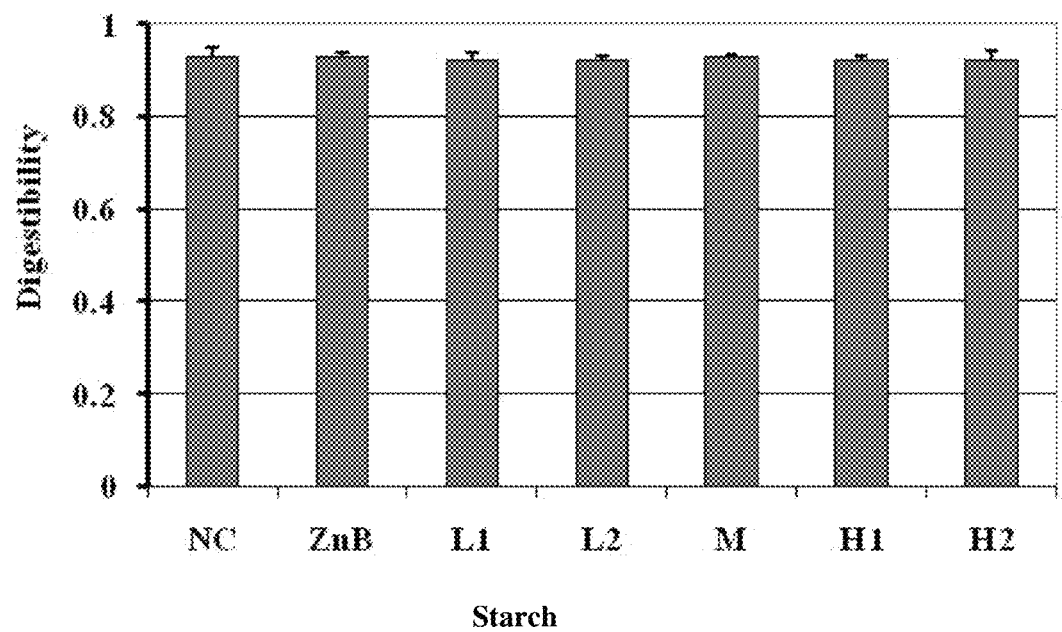
Figure 4C:
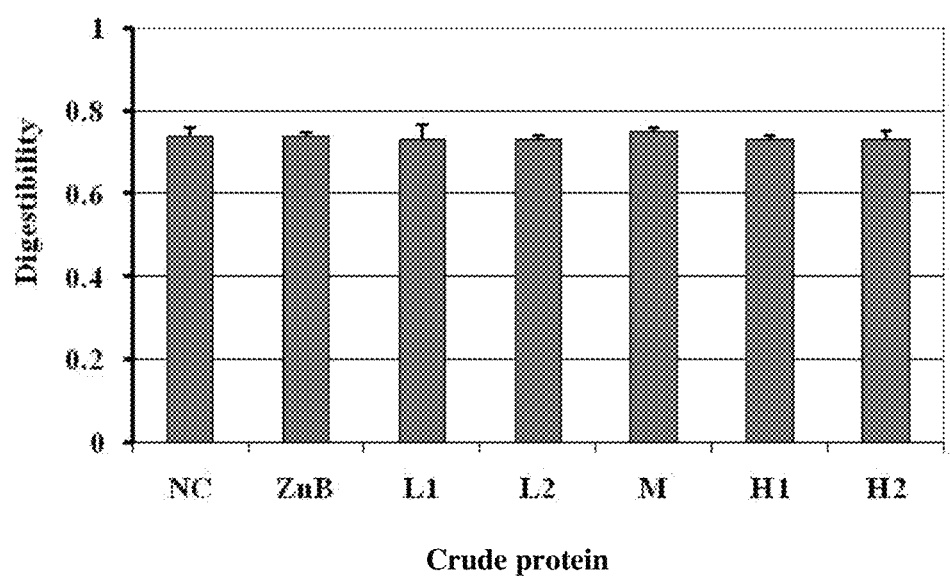
Figure 5A:
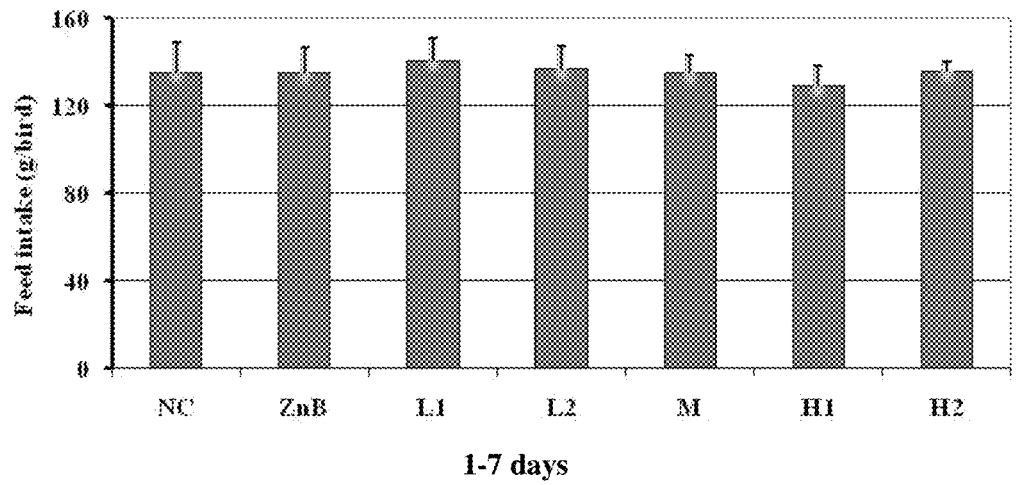
FIGS. 5A, 5B, 5C and 5D: Feed consumption from hatch to different points of age.
Figure 5B:
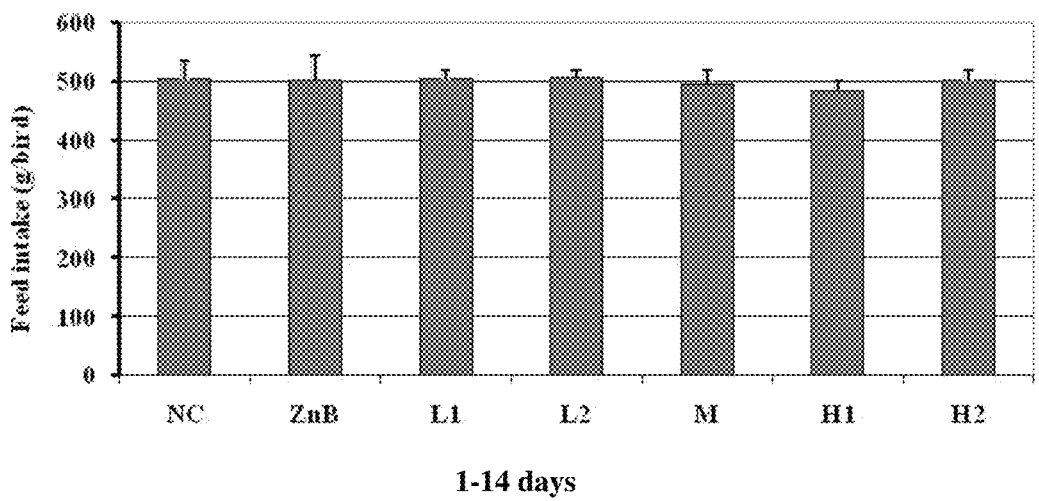
Figure 5C:
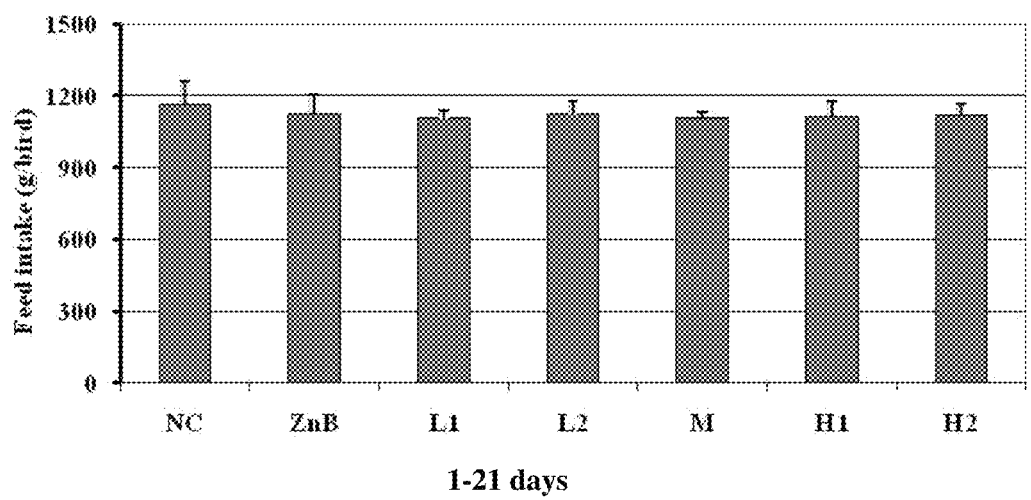
Figure 5D:
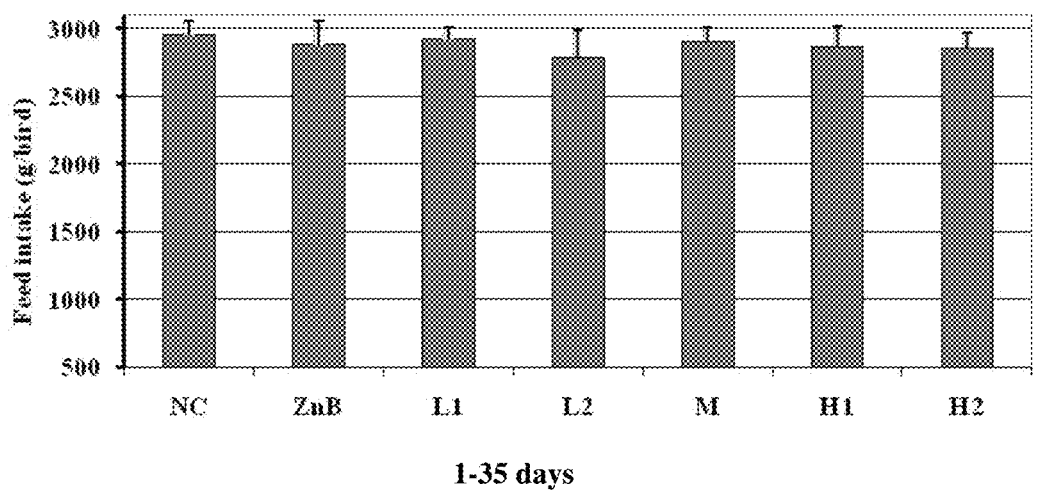
Figure 6A:
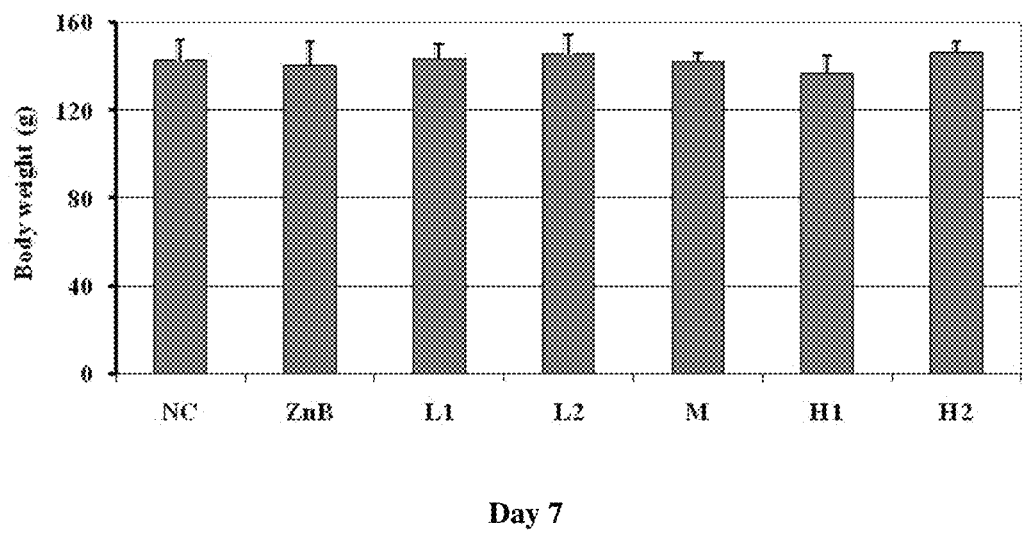
FIGS. 6A, 6B, 6C and 6D: Body weight at different points of age.
Figure 6B:
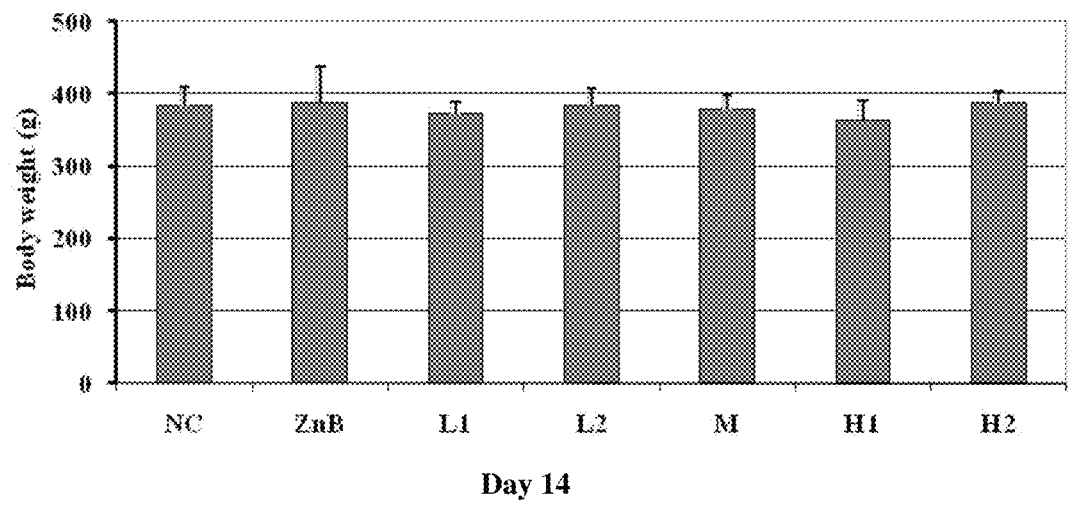
Figure 6C:
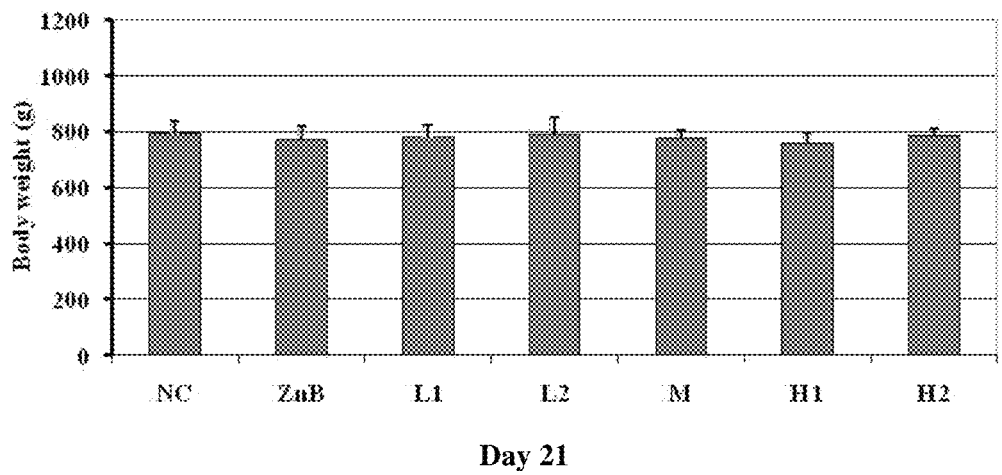
Figure 6D:
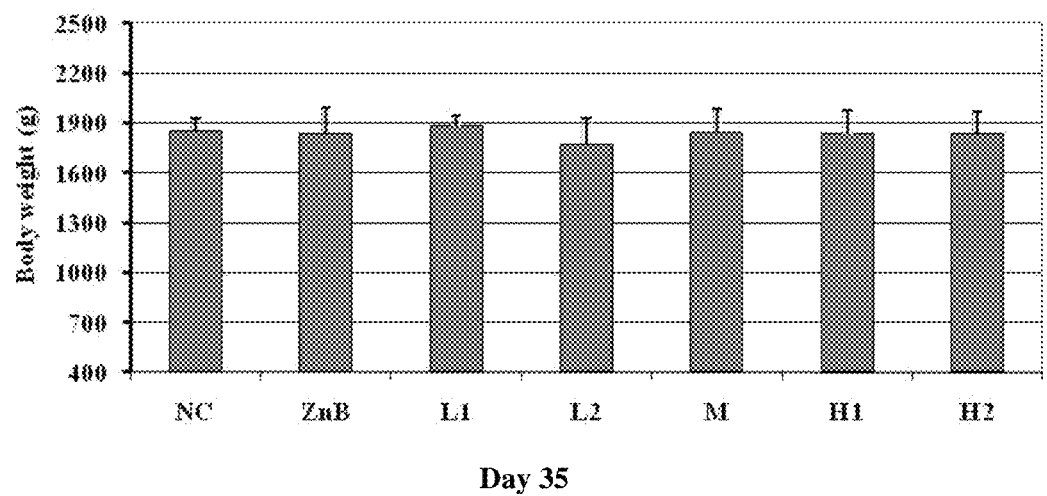
Figure 7A:
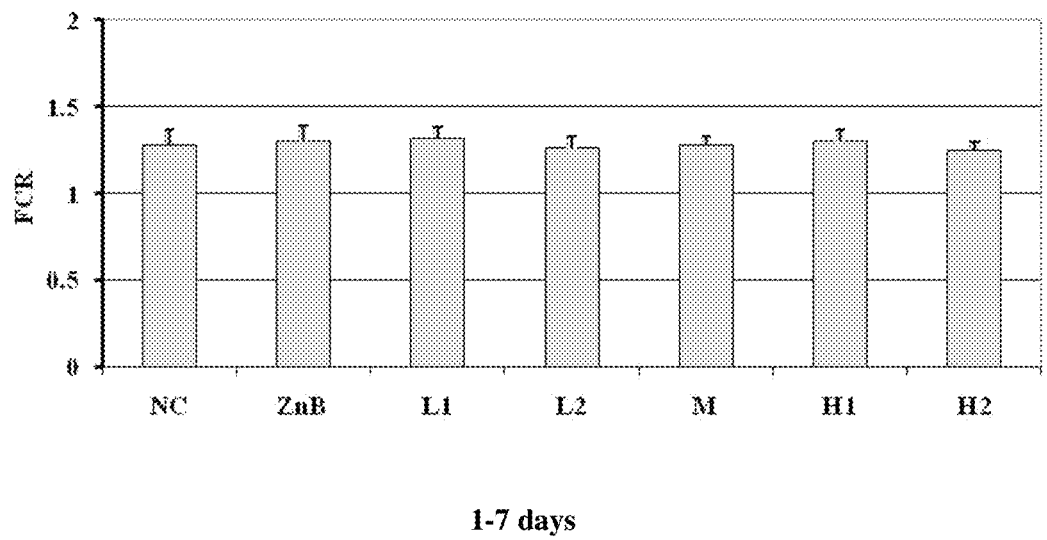
FIGS. 7A, 7B, 7C and 7D: Feed conversion ratio (FCR) from hatch to different points of age.
Figure 7B:
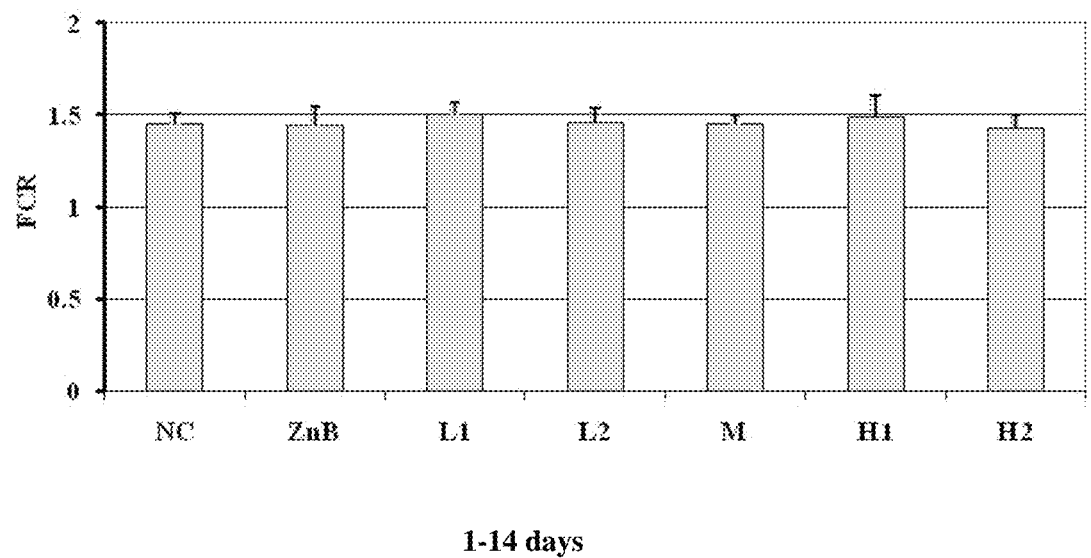
Figure 7C:
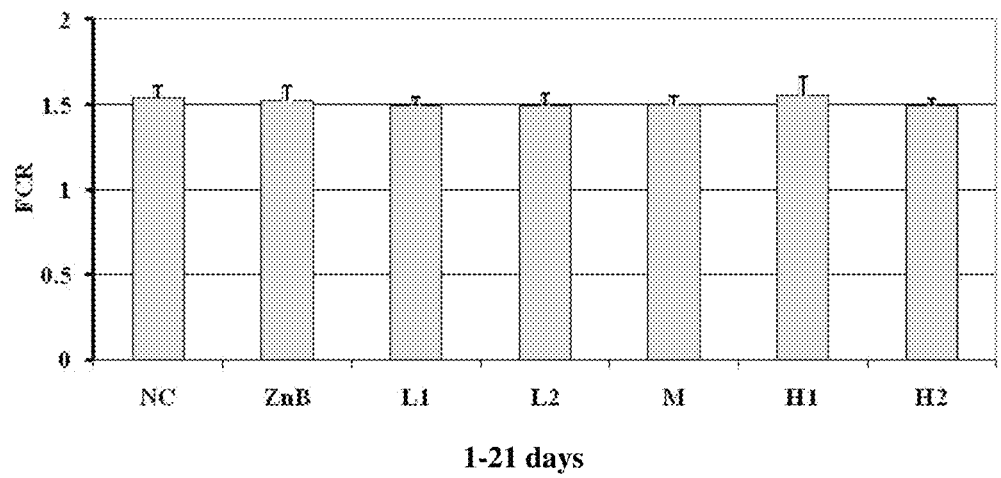
Figure 7D:
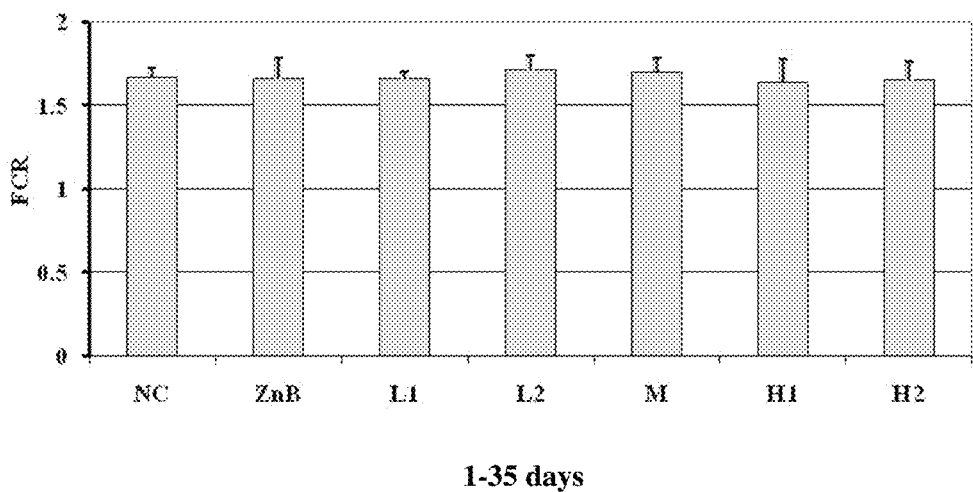

Table 1: Randomization of replicates in Experiment 1 (measured effects of tea tree oil supplementation on productivity).

Table 2: Concentration (ppm) of tea tree oil, by headspace GCFID, in meat and manure samples collected at 34 days of age.

Table 3: Randomization of replicates in Experiment 2 (measured gut microbial profiles).

Table 4: Relative weight (g/100 g body weight) of visceral organs at 7 and 21 days of age of chicks fed tea tree oil supplemented diets.

Table 5: Distribution and causes of mortality/culls in Experiment 2 (measured gut microbial profiles).

Table 6: Populations of key microbial groups and species (Log CFU/g digesta) in the ileum and at 21 and 35 days of age.

Table 7: Populations of key microbial groups and species (Log CFU/g digesta) in the caeca at 21 and 35 days of age.

Table 8: Concentrations of SCFAs (μmol/g digesta) in the caeca at 21 and 35 days of age.

Table 9: Randomization of replicates in Experiment 3 (measured prophylactic potential of tea tree oil).

Table 10: Distribution and causes of mortality/culls in Experiment 3 (measured prophylactic potential of tea tree oil).

Table 11: Populations of key microbial groups and species (Log CFU/g digesta) in the ileum at 21 and 35 days of age.

Table 12: Populations of key microbial groups and species (Log CFU/g digesta) in the caeca at 21 and 35 days of age.

Table 13: Concentrations of SCFAs (μmol/g digesta) in the caeca at 21 and 35 days of age.

DETAILED DESCRIPTION OF THE INVENTION

The present invention provides a feed composition for an animal comprising tea tree oil wherein the tea tree oil is present in an amount sufficient to reduce bacterial infection in the animal upon ingestion of the feed composition.

Tea tree oil is a natural oil derived from a tree of the genus *Melaleuca*, especially from the species *Melaleuca alternifolia*. It has been defined in the art by international standard ISO 4730:2004 ("Oil of *Melaleuca*, terpinen-4-ol type (Tea Tree oil)"), which specifies levels of 15 different components present in tea tree oil. Amongst its many components, at least terpinen-4-ol is believed to provide a level of antimicrobial activity.

In one embodiment the tea tree oil is present in the feed composition at an amount of between 2 milligrams and 70 milligrams per kilogram of the composition. For example, the amount of tea tree oil in the feed composition may be selected from about 2, 3, 4, 6, 8, 12, 16, 24, 32, 35, 48, 50 and 65 milligrams per kilogram of diet.

As used herein, the term "about", unless stated to the contrary, refers to +/−20%, more preferably +/−10%, of the designated value. For the avoidance of doubt, the term "about" followed by a designated value is to be interpreted as also encompassing the exact designated value itself (for example, "about 20" also encompasses 20 exactly).

In another embodiment the feed composition further comprises a carrier agent for the tea tree oil.

In one embodiment the carrier agent for the tea tree oil is an oil.

In one embodiment the carrier agent for the tea tree oil is a vegetable oil. The vegetable oil may be, for example, rapeseed oil or canola oil.

In one embodiment the carrier agent for the tea tree oil is canola oil. The canola oil may be present in an amount of 20 ml per 1 kg of composition, or in any other amount as described herein.

In one embodiment the tea tree oil is encapsulated by an encapsulating agent.

In one embodiment, the encapsulating agent is a cyclodextrin. Cyclodextrins (also known as cycloamyloses, cyclomaltoses, or Schardinger dextrins) are cyclic oligosaccharides comprising a number of glucopyranose subunits linked by α-(1,4) bonds (see, e.g., Del Valle, E. M. (2003), Astray, G. et al., (2009)). α-cyclodextrins consist of six glucopyranose units, β-cyclodextrins consist of seven glucopyranose units, γ-cyclodextrins consist of eight glucopyranose units, and δ-cyclodextrins consist of nine glucopyranose units. Any cyclodextrin can be used in the present invention. β-cyclodextrins are preferred since they are currently the simplest to purify and therefore, the cheapest to produce. Cyclodextrins are formed by the intramolecular transglycosylation of hydrolysed starch, a reaction which is catalysed by the enzyme cyclodextrin glucosyl transferase. In addition to naturally occurring cyclodextrins, many derivatives have been synthesised (for example, by aminations, esterifications or etherifications of primary and secondary hydroxyl groups). Both naturally occurring and synthetic cyclodextrins, and derivatives thereof, can be used in the present invention.

The cyclic, toroidal structure of cyclodextrins presents a hydrophilic outer surface and a relatively hydrophobic inner surface, which allows these compounds to encapsulate a wide variety of molecules to form inclusion complexes. Each cyclodextrin molecule is capable of acting as a "host molecule", encapsulating a single "guest" molecule, and consequently, cyclodextrins are often referred to as microencapsulating agents.

Cyclodextrins have been used in a wide variety of applications, including in pharmaceuticals as solubilizers, diluents or additives to improve the physical and chemical properties and bioavailability of drugs; in cosmetics to suppress the volatility of perfumes; in the agricultural industry to form complexes with a variety of agricultural chemicals such as herbicides and insecticides; in the chemical industry to separate isomers and enantiomers, to catalyse reactions and to remove or detoxify waste materials; and in food formulations for flavour protection and/or flavour delivery (since many artificial flavours are volatile oils or liquids) (Del Valle, E. M. (2003)). Cyclodextrins are widely recognised as safe for use in foods, and α, β and γ-cyclodextrins have been added to the GRAS list ("generally recognised as safe") by the US FDA.

Cyclodextrins have also been used successfully to encapsulate tea tree oil. For example, Wacker Chemie AG provides a β-cyclodextrin for the encapsulation of tea tree oil under the trademark CAVAMAX®. Thus, CAVAMAX® can be used as an encapsulating agent in the present invention. More generally, any commercially available cyclodextrin can be used in the present invention.

One advantage of the use of a cyclodextrin to encapsulate tea tree oil in the present invention is the increased thermal stability and shelf-life stability an inclusion complex comprising tea tree oil and a cyclodextrin provides. Thus, less tea tree oil will be lost during the production of a feed composition of the invention, and less tea tree oil will be lost after production of the feed composition.

Tea tree oil can be encapsulated by a cyclodextrin by any means known in the art. For example, the tea tree oil can simply be added to a cyclodextrin solution and mixed. Other suitable methods will be apparent to the person skilled in the art. It will be appreciated that not all of the tea tree oil in the feed composition may be encapsulated by such methods. Thus, the invention provides a feed composition wherein at least 25%, at least 50%, at least 70%, at least 80%, at least 90%, or at least 95% of the tea tree oil is encapsulated. A desired amount of encapsulated tea tree oil may be achieved by adapting such methods using routine experimentation and analysis.

The feed composition for an animal according to the present invention comprises food stuff for animals in combination with tea tree oil that is present in an amount sufficient to reduce bacterial infection.

Food stuff for animals includes grain based feeds, such as poultry feed, and may include cereal grains, soybeans, oil seeds, etc.

In one example the feed composition comprises tea tree oil, wheat, sorghum, mung beans, tallow, canola meal, cottonseed meal, soybean meal, meat and bone meal, lysine, methionine, vitamins, trace minerals and zinc bacitracin.

In one embodiment the feed composition maintains levels of feed consumption, body weight, efficiency of feed utilisation, and gut microbial profile of the animal.

By 'gut microbial profile' we mean the natural microbial cultures residing in the gut and maintaining health by aiding proper digestion and/or supporting immune system function.

The present invention also provides a method of protecting animals from bacterial infection comprising feeding the animals with a diet comprising tea tree oil at an amount sufficient to reduce bacterial infection in the animal. The method may comprise feeding the animal with any embodiment of the feed composition as described herein.

The efficiency of tea tree oil to reduce bacterial infection in an animal may be measured by any suitable means. For example, the animal may be challenged by a microbial agent such as *Salmonella sofia*. The effect of tea tree oil in reducing bacterial infection in the challenged animal may be measured by the levels of short chain fatty acids (SCFA). SCFA are end products of bacterial metabolism and are therefore suitable for assessing the level of gut microbial activity.

The term 'treated animal' is defined as an animal that is fed a diet comprising tea tree oil in an amount sufficient to reduce bacterial infection.

In one embodiment the method of protecting the animal comprises feeding the diet in a feeding regime comprising a starter diet and a finisher diet.

For example, when the diet is fed to chickens, the starter diet may be fed from day 0 to day 21 of a chick's life, and the finisher diet may be fed from day 21 to day 35 of the chick's life. Alternatively, chicks may be fed a finisher diet beyond 35 days of their lives. For example, the finisher diet may be fed from day 21 to day 42 of the chick's life.

In another embodiment the method involves feeding the animal tea tree oil at an amount of between 2 milligrams and 65 milligrams per kilogram of diet.

The method of protecting the animal may also comprise feeding a diet wherein tea tree oil is present at an amount of between 2 milligrams and 32 milligrams per kilogram of the starter diet. For example, the amount of tea tree oil in the starter diet may be selected from about 2, 4, 8, 16, 32, 35, 50 and 65 milligrams per kilogram of diet.

The method of protecting the animal may also comprise feeding a diet wherein tea tree oil is present at an amount of between 3 milligrams and 65 milligrams per kilogram of the finisher diet. For example, the amount of tea tree oil in the finisher diet may be selected from about 3, 6, 12, 24, 32, 35, 48, 50 and 65 milligrams per kilogram of diet.

The present invention also provides a method of preparing a feed composition comprising the steps of
(a) combining tea tree oil with a vegetable oil, and
(b) combining (a) with a feed composition.

The method of preparing the feed composition may involve combining tea tree oil in an amount of between 2 and 70 milligrams with vegetable oil. The tea tree oil may be combined with between 20,000 and 30,000 milligrams of vegetable oil.

In one embodiment the vegetable oil is canola oil.

In another embodiment the method of preparing the feed composition comprises the step of combining tea tree oil with canola oil at least 12 hours, preferably at least 24 hours prior to the step of combining the tea tree oil/canola oil mixture with the feed composition.

For example, the amount of tea tree oil required for the feed composition (which may be, for example, from 2 to 70 milligrams per kilogram) may be mixed with 200 ml of canola oil. Twenty-four hours after this mixture is prepared, it may be uniformly incorporated into a small batch of the diet (or "feed composition"), for example 5 kg, before being mixed with the bulk of the diet.

The mixture of tea tree oil and vegetable oil may be combined with the feed composition using any suitable means. For example, the mixture and the feed composition may be mixed in any suitable mixing apparatus, such as a paddle blade mixer, for example a Tatham Forberg mixer. The tea tree oil and vegetable oil mixture may be mixed together with the feed composition for any period of time suitable to ensure a reasonably uniform dispersion of the tea tree oil and vegetable oil mixture in the feed composition.

The method of the invention may further comprise a step of encapsulating the tea tree oil in an encapsulating agent. The tea tree oil may be encapsulated in an encapsulating agent at any suitable stage during the method of preparing the feed composition. For example, the tea tree oil may be encapsulated before or after combination with a vegetable oil. Preferably, the tea tree oil is encapsulated before combination with a vegetable oil. Thus, the tea tree oil in step (a) of the method described herein may be encapsulated by an encapsulating agent.

The diet may comprise conventional additives, such as flavourings, and a conventional absorbing support. For example, the absorbing support may contain one or more additives selected from stearin, curcuma powder, rosemary powder, limestone, a gum, such as gum Arabic, sugar and/or starch and water.

The diet may also comprise vitamins, enzymes, mineral salts, ground cereals, protein-containing components, carbohydrate-containing components, wheat middlings and/or brans.

For example, the cereals incorporated in the diet may include ground or crushed wheat, oats, barley, maize and rice.

The method of the invention may further comprise a step of forming the feed composition into pellets. This step may be performed after the tea tree oil and vegetable oil mixture has been combined with the feed composition, and may be performed whether or not the tea tree oil has been encapsulated. The encapsulation of the tea tree oil as defined herein has the particular advantage that less tea tree oil is lost during the pelleting process.

Any known process of forming pellets may be used. The process may convert a feed composition in the form of a finely or coarsely ground blend of components into a dense agglomerate or pellet by compaction under pressure, for example, using a roll and die apparatus. The particular parameters of the apparatus used may be adjusted in order to produce the desired size and density of pellets. In addition, particular components (such as grains, milled grain by-products, fats, pellet binders, minerals, etc.) may be included in the feed composition in order to affect the 'pelletability' of the composition (see, e.g., MacBain, (1966) and Bartikoski, (1962)).

The pelleting process may be carried out at any temperature. For example, the feed composition may be hot pelleted by conditioning the feed composition at high temperature and pelleting at a high temperature. For example, the feed composition may be conditioned at about 65° C., 75° C. or 85° C. and may be pressed (or 'pelleted') at about 65° C., 75° C., 85° C., or at 1, 2, or 3 degrees above these temperatures. The temperature at which the feed composition is conditioned may be selected independently of the temperature at which the feed composition is pressed. Thus, any combination of suitable temperatures for feed conditioning and feed pelleting may be selected.

The feed composition may be conditioned at a high temperature for any suitable time period. For example, the feed composition may be conditioned at a high temperature for about 10, 15, or 20 seconds. In one example, the feed composition is conditioned at a high temperature for 15 seconds.

The feed composition may be pressed under any suitable pressure. For example, the feed composition may be pressed at 2, 3 or 4 bar. In one example, the feed composition is pressed at 3 bar.

In one example, the feed composition of the invention is hot pelleted by conditioning the feed composition to 85° C. for 15 seconds immediately prior to pelleting under 3 bar pressure. These conditions represent the European standard for hot-pelleting chicken feed.

In order that the nature of the present invention may be more closely understood preferred forms thereof will now be described with reference to the following Examples.

WORKING EXAMPLES

Three experiments were conducted to evaluate the potential benefits of tea tree oil (TTO) in diets for chickens. In the first experiment, the effects of TTO on the feed intake, body weight, feed conversion ratio (FCR), intestinal development and growth of selected visceral organs in broiler chickens were investigated. The presence of residues of TTO in the meat and manure (litter and faeces) was also evaluated as part of this study. In the second experiment, changes in microbial profiles of the gut and products formed by such microbes were assessed. The third experiment was a disease challenge trial in which the potential of TTO to protect chickens under infection from *Salmonella sofia* was tested.

Materials and Methods

Tea Tree Oil

The tea tree oil used in the studies had the following properties:
Name: Tea Tree Oil
Purpose of use: Feed supplement
Appearance: Clear Liquid
Purity: 100%
Storage condition: Room Temperature, in the dark.
The composition of the tea tree oil used was:

|  | Sample ID | |
| --- | --- | --- |
| Lab No | 1222 15605 | ISO4730 RANGE % |
| 1. α-pinene % | 2.4 | 1-6 |
| 2. sabinene % | 0.3 | tr-3.5 |
| 3. α-terpinene % | 9.6 | 5-13 |
| 4. limonene % | 1.1 | 0.5-1.5 |
| 5. p-cymene % | 2.6 | 0.5-8 |
| 6. 1,8-cineole % | 3.8 | tr-15 |
| 7. γ-terpinene % | 21.1 | 10-28 |
| 8. terpinolene % | 3.4 | 1.5-5 |
| 9. terpinen-4-ol % | 42.0 | 30-48 |
| 10. α-terpeniol % | 3.1 | 1.5-8 |
| 11. aromadendrene % | 0.9 | tr-3 |
| 12. ledene % | 0.5 | tr-3 |
| 13. δ-cadinene % | 0.7 | tr-3 |
| 14. globulol % | 0.1 | tr-1 |
| 15. viridiflorol % | 0.2 | tr-1 |

(where 'tr' means a trace amount).

Zinc Bacitracin

Zinc Bacitracin is an antibacterial polypeptide that is an accepted form of antibiotic to be included in feed compositions for animals and was incorporated into the study to determine the effects of tea tree oil compared to an industry standard antibacterial agent. It was obtained from Ridley Agriproducts and had the following properties:
Product Name: ALBAC 150G Antibiotic Feed Premix
Chemical Names: Dried fermentate containing bacitracin zinc
Poisons Schedule: S4 Bacitracin>2%
Purpose of use: Feed supplement; positive control
Appearance: Yellow-gray powder. Not soluble in water.
Density: Approx. 650 kg/m$^3$
Ingredients: 15% Bacitracin zinc
    <10% Other ingredients
    to 100% Dried fermentate
Storage condition: Room Temperature Canola Oil Canola oil was used as the vehicle to deliver the tea tree oil and zinc bacitracin in the animals' diets. Canola oil was obtained from standard commercial outlets 1-2 days before each feed mixing. The properties of the canola oil are as follows:
Name: Home Brand Canola Oil
Purpose of use: Vehicle
Appearance: Pale yellow
Purity: 100%
Storage condition: Room Temperature Experimental Animals The animals used to test the feed supplement properties of tea tree oil were broiler chicks of the Cobb strain. Day-old chicks of mixed sexes that had been vaccinated against Marek's disease, infectious bronchitis and Newcastle disease were obtained from Baiada Hatchery, Kootingal NSW, Australia.

The weight of the chicks at commencement of the feed supplement studies were 39.8±0.66 g for Experiment 1 (which measured the effects on productivity), 39.9±0.73 g for Experiment 2 (which measured gut microbial profiles) and 47±1.06 g for Experiment 3 (which measured prophylactic properties of tea tree oil).

Diets

The tea tree oil was provided in the diets of the animals in a feeding regime consisting of two basal diets, a starter diet and a finisher diet. The starter diet was fed from day 0 to day 21 of a broiler chick's life and the finisher diet was fed from day 21 to day 35 of a broiler chick's life. Twenty-one days of age represents a milestone in feeding of broiler chickens in many countries. The second milestone of thirty-five days of age is relevant as the marketing age for the whole chicken market. The compositions of the basal starter and finisher diets were:

|  | Starter diet (1-21 d) | Finisher diet (22-35 d) |
| --- | --- | --- |
| Ingredient (g/kg) | | |
| Wheat | 262.0 | 214.0 |
| Sorghum | 350.3 | 400.0 |
| Mung beans | 100.0 | 100.0 |
| Tallow in mixer | 32.5 | 34.0 |
| Canola meal | 60.0 | 25.0 |
| Cottonseed meal | 0.0 | 50.0 |
| Soybean meal | 157.0 | 81.5 |
| Limestone | 15.5 | 16.0 |
| Kynofos | 11.5 | 11.0 |
| Salt | 1.75 | 1.5 |
| Sodium bicarbonate | 2.0 | 2.0 |
| Choline chloride | 0.6 | 0.6 |
| DL-Methionine | 2.1 | 1.3 |
| L-Lysine | 2.1 | 0.4 |
| L-Threonine | 0.2 | 0.0 |
| Premix | 2.0 | 2.0 |
| Rovimix (Vitamin C) | 0.1 | 0.1 |
| Ronozyme WX CT | 0.25 | 0.25 |
| Ronozyme P5000 Broiler | 0.15 | 0.15 |
| Nutrient composition (g/kg) | | |
| ME (MJ/kg) | 12.2 | 12.4 |
| Crude protein | 200.0 | 190.0 |
| Fat | 52.2 | 54.5 |
| Calcium | 9.7 | 9.8 |
| Available phosphorus | 4.6 | 4.5 |
| Lysine | 11.5 | 8.8 |
| Methionine | 5.0 | 4.2 |
| Methionine + Cysteine | 8.3 | 7.4 |
| Threonine | 7.4 | 6.8 |
| Leucine | 16.6 | 15.8 |
| Isoleucine | 8.5 | 7.7 |
| Tryptophan | 2.3 | 2.3 |
| Linoleic acid | 9.8 | 10.4 |
| Choline (mg/kg) | 1494.7 | 1499.9 |

In both the starter and finisher diets, tea tree oil was initially mixed with the canola oil. In one embodiment the required amount of tea tree oil was mixed with 200 ml of canola oil. Twenty four hours after the tea tree oil is mixed with canola oil, this is mixed with approximately 5 kg of feed composition, before being mixed with bulk of the diet. The amount of tea tree oil added to the feed composition was altered according to the amounts shown in Table 1 below. Briefly, the level of tea tree oil in the starter diet ranged from 2 mg/kg to 32 mg/kg. The level of tea tree oil in the finisher diet ranged from 3 mg/kg to 48 mg/kg. The levels of inclusion of tea tree oil shown in Table 1 were calculated to deliver specified amounts of tea tree oil in accordance with feed consumption at different stages of growth of the animals.

The negative control feed containing the canola oil vehicle only was similarly prepared, replacing tea tree oil with canola oil.

The feed composition with zinc bacitracin was prepared in a similar manner to the feed composition containing tea tree oil. Zinc bacitracin was used at a constant recommended incorporation rate of 50 mg/kg. The antibiotic containing feed composition was fed in both the starter diet and the finisher diet.

A single batch of starter and finisher feed was prepared for each dose group. The prepared feed was stored at ambient temperature during feeding. The feeding trial started within 5 days of mixing the diets.

Birds were fed on ad libitum basis, with feed troughs filled to about three-quarters of volume. The feed troughs were refilled with diet as required.

Statistical Analysis

Data were subjected to one-way analysis of variance for completely randomized design and tested for significance between the dietary treatment means (Minitab, version 15). Differences were considered significant at $P \leq 0.05$.

Example 1—Effects on Productivity of Broiler Chickens when Tea Tree Oil is Added to Chicken Feed 1.1—Experimental Protocol 1.1.1 Birds and Management Three hundred and thirty-six mixed-sex chicks (initial weight, 39.8±0.66 g) were randomly allocated to 7 treatments of 6 replicates (8 birds per replicate). The seven treatments were a negative control diet, a positive control containing zinc bacitracin (50 ppm), and the same diet supplemented with tea tree oil (TTO) at 2, 4, 8, 16 or 32 mg/kg diet during the starter phase (1-21 days), or 3, 6, 12, 24 or 48 mg/kg diet in the finisher phase (22-35 days). These diets were designated NC, ZnB, L1, L2, M, H1 and H2, respectively. For the first three weeks, the birds were reared in brooder cages (600×420×230 cm) with a wire floor in environmentally controlled experimental rooms. The temperature was set at 33° C. for the first three days and gradually reduced to 24° C. at 21 d of age. At 21 days, the birds were transferred to larger battery cages (800×740×460 cm) and the temperature was maintained at 23-24° C. Lighting was provided for 24 hours on the first day and thereafter for 18 hours per day. Chickens had ad libitum access to feed and water.

A total of five tea tree oil treatment groups were utilised in the study, along with a negative control (vehicle only) and a positive control (zinc bacitracin). Information on the treatment groups, dose levels and bird numbers are presented in Table 1. Celite (acid insoluble ash, 5 g/kg) was added to the diets as a marker to enable measurement of nutrient digestibility.

TABLE 1

Randomization of replicates in Experiment 1

| Treatment Group | Code | Dose (mg/kg) Starter (0-21 d) | Dose (mg/kg) Finisher (21-35 d) | Replicate No. |
|---|---|---|---|---|
| Negative Control (vehicle) | NC | 0 | 0 | 1, 8, 21, 28, 32, 36 |
| Positive Control (Zn Bacitracin, ppm) | ZnB | 50 | 50 | 2, 13, 19, 22, 31, 37 |
| TTO (mg/kg diet) | L1 | 2 | 3 | 3, 9, 15, 27, 29, 38 |
|  | L2 | 4 | 6 | 4, 10, 16, 26, 30, 39 |
|  | M | 8 | 12 | 5, 11, 17, 23, 34, 40 |
|  | H1 | 16 | 24 | 6, 12, 18, 24, 35, 41 |
|  | H2 | 32 | 48 | 7, 14, 20, 25, 33, 42 |

On day 21, four chicks were selected at random from each replicate and euthanized by cervical dislocation. Each bird was dissected and the contents of the ileum were pooled within a pen and frozen immediately for assessment of nutrient digestibility.

The digesta samples were freeze-dried and ground for further analyses. The diets and freeze-dried digesta were analyzed for gross energy by bomb calorimeter (IKA C7000 calorimeter, IKA-Werke, Staufen, Germany), crude protein by nitrogen analyzer (Leco FP 2000, protein/nitrogen analyzer, Michigan, USA) and starch by Megazyme total starch assay. The concentrations of acid-insoluble ash (AIA) in the diet and digesta were measured. The apparent digestibility coefficient of the nutrients was then calculated from the equation:

$$1 - ((\text{ileal nutrient/ileal AIA})/(\text{diet nutrient/diet AIA})).$$

On day 34, about 50 g of manure (faeces and litter) and half a breast of chicken were collected from each replicate, frozen and analysed for any residue of tea tree oil and metabolites.

1.1.2 Observations

Body weight and feed intake were recorded at weekly intervals. Twice daily, birds were monitored for mortality and in the event of mortality, dead birds were removed from the cage and a record made in the study files; dead birds were subjected to gross pathology. Clinical observations were made on a daily basis and any abnormal behaviour was similarly documented.

1.1.3 Residue Analysis

The meat and manure samples were prepared for analysis by extraction into a 0.5% acetone aqueous solution, followed by agitation and sonification. Each replicate analysis lasted 120 minutes, with 50 minutes of incubation and 70 minutes of gas chromatography. Gas chromatography was performed on an Agilent 6890 machine installed with an SGE 60 m, 0.22 mm, 0.1 μm film, BPX5 column with headspace extraction on an Agilent 7694 head space analyser. The external standard, Terpinen-4-ol, used was supplied by Fluka Chemicals while the internal standard, tridecane, was supplied by Sigma. For method development, blank control chicken meat and manure were acquired from the local supermarket and home-fed chicken shed, respectively. The method was validated and assessed for repeatability, accuracy and specificity.

1.2—Results 1.2.1 Feed Consumption

Feed consumption was recorded at weekly intervals during the course of the study until slaughter (day 34). Individual and mean data (for replicates and groups) are presented in FIG. 1.

The test supplement had no effect (P>0.05) on feed consumption of chicks between hatch and 34 days of age (FIG. 1). Up to 7 days of age, the supplement, at the lowest level of inclusion (2 mg/kg; L1) induced a 6% increase in feed consumption when compared to the negative control group (NC). Over subsequent periods, the same level of supplement resulted in increases in feed consumption of about 3, 6 and 4% up to days 21, 28 and 34, respectively. On the positive control diet (ZnB), feed consumption was 1, 2 and 2% lower than that on the NC diet up to 7, 21 and 34 days, respectively. Feed intake to 28 days on the ZnB diet was lower but similar to that on the control diet. Over the entire test period (34 days), the test supplement tended to increase feed consumption except at the L2 level, in which feed consumption was reduced by about 4%.

1.2.2 Body Weight

Body weight was recorded at the start of the study (day 1) and at weekly intervals thereafter, and at slaughter. Individual bodyweights and mean bodyweights (for replicates and groups) are presented in FIG. 2.

The body weight of chicks was not significantly (P>0.05) affected by the test supplement over any of the time periods tested. Compared to the NC diet, the supplement increased the 7-day body weight by 2.5 and 3% at L1 and M, respectively but reduced weight by about 2.5 and 1% at L2 and H2 over the same test period (7 days). The positive control diet (ZnB) improved the 7-day body weight by 2% compared to the NC diet. At 21 days of age, chicks on the L1 diet were 6% heavier than those on the NC diet. The improvement on the H1 and H2 diets was about 4 and 1%, respectively while the 21 day weight of the L2 and M groups was reduced. The ZnB diet did not improve weight at 21 days. At 34 days of age, the final weight of the chicks on the diets supplemented with TTO was generally higher (by up to 7.5 and 6% on H1 and L1 diets), respectively than on the NC diet. However, there was a 1.5% reduction in the 34 day weight of L2 group. The ZnB diet improved final weight by only 1%.

1.2.3 Feed Conversion Ratio

Feed conversion data are presented in FIG. 3. The test agent improved the feed conversion ratio (FCR) to 7 days only at M and H1 levels of inclusion but this was not significantly (P>0.05) different from the response on other diets (FIG. 3). Up to this age, the ZnB diet improved FCR by 3.5%. From hatch to 21 days of feeding, TTO generally improved (P>0.05) FCR by between 0.5 and 3.4%, compared to 1.7% on the ZnB diet. Over the entire feeding period (1-34 days), TTO improved FCR by up to 4%, the lowest improvement being 2.2%. The improvement on the ZnB diet was 3.3%.

1.2.4 Mortality and Culls

In general, the batch of chicks used in this study was healthy and remained largely so during the trial. One chick from Group M died during the experiment (day 17). Three other chicks from Groups L1 (day 25), L2 (day 25) and ZnB (day 27), were culled due to ill health. No abnormal behavioural or clinical observations were recorded during the study.

1.2.5 Residue of Test Agent in Manure and Meat

Residues of the test agent were not detected in the breast meat obtained from 34 day-old chicks (Table 2). The residue was also not detected in the manure when fed up to 4 mg/kg diet (L2). Beyond this concentration, the residue appeared in manure at a concentration of less than 0.5, 0.5 and 0.9 ppm in the M, H1 and H2, respectively.

TABLE 2

Concentration (ppm) of tea tree oil, by headspace GCFID, in meat and manure samples collected at 34 days of age.

| Treatment | Starter diet | Finisher diet | Meat | Manure |
| --- | --- | --- | --- | --- |
| Negative control | — | — | nd | nd |
| Positive control | — | — | nd | nd |
| TTO, L1 | 2 | 3 | nd | nd |
| TTO, L2 | 4 | 6 | nd | nd |
| TTO, M | 8 | 12 | nd | <0.5 |
| TTO, H1 | 16 | 24 | nd | 0.5 |
| TTO, H2 | 32 | 48 | nd | 0.9 | nd—Not detected.

Example 2—Gut Microbial Profiles of Broiler Chickens on Diets Supplemented with Tea Tree Oil

2.1—Experimental Protocol

2.1.1 Birds and Management

Three hundred and thirty-six mixed-sex chicks (initial weight, 39.9±0.73 g) were also used in this study, mainly to investigate changes in intestinal microbial profiles. The experimental design was exactly as described for Experiment 1, except that the chicks were sexed before allocation to the treatment groups. Each replicate contained five females and three males. During sample collection for assessment of early organ development on day 7, only female birds (one per replicate) were chosen; at 21 days, two females and a male were chosen per replicate, and the remaining birds (usually 2 of each sex) were slaughtered at 35 days of age. Samples were collected at days 21 and 35 principally for the assessment of intestinal microbial profiles and short-chain fatty acids (SCFAs), although gross changes (feed consumption, weight gain and nutrient digestibility) in the population were also monitored on a weekly basis. On days 7 and 21, the weight of key visceral organs, including the proventriculus, gizzard, small intestine, pancreas, liver, yolk sac (day 7 only), spleen (day 21 only) and the bursa of Fabricius was recorded and related to body weight. The spleen and bursa serve very important immune functions in poultry. Only female birds were involved in this assessment. Mortality was recorded as it occurred and feed intake was adjusted appropriately. Information on the treatment groups, dose levels and bird numbers are presented in Table 3. Celite (acid insoluble ash, 5 g/kg) was added to the diets as a marker to enable measurement of nutrient digestibility.

TABLE 3

Randomization of replicates in Experiment 2

| | | Dose | | |
| --- | --- | --- | --- | --- |
| Treatment Group | Code | Starter (0-21 d) | Finisher (21-35 d) | Replicate No. |
| Negative Control (vehicle) | NC | 0 | 0 | 1, 4, 14, 22, 25, 35 |
| Positive Control (Zn Bacitracin, ppm) | ZnB | 50 | 50 | 2, 10, 15, 23, 31, 36 |
| TTO (mg/kg diet) | L1 | 2 | 3 | 8, 12, 16, 29, 33, 37 |
| | L2 | 4 | 6 | 3, 13, 17, 24, 34, 38 |
| | M | 8 | 12 | 5, 6, 19, 26, 27, 40 |
| | H1 | 16 | 24 | 7, 11, 20, 28, 32, 41 |
| | H2 | 32 | 48 | 9, 18, 21, 30, 39, 42 |

2.1.2 Microbial Assessment

Culture-based microbiology analyses were conducted to quantitatively measure the population of Lactobacilli (Rogosa agar, Oxoid, Hampshire, UK), lactose negative enterobacteria and coliforms (on MacConkey agar, Oxoid, Hampshire, UK), lactic acid bacteria (MRS agar, Oxoid, Hampshire, UK), total anaerobic bacteria (Wilkins-Chalgren agar, Oxoid, Hampshire, UK), and *Clostridium perfringens* (*C. perfringens* TSC agar, Oxoid, Hampshire, UK). Samples were serially diluted and spread onto each agar. All agars were incubated at 39° C. for between 1 and 7 days, depending on the agar.

2.1.3 Concentrations of Short-Chain Fatty Acids

Short-chain fatty acids were analysed by gas chromatography (GC, Model CP 3800, Varian Analytical Instruments, Palo Alto, Calif., USA). Approximately 2 to 3 g of thawed digesta were suspended in 3 mL of 0.1 M sulphuric acid in a screw-capped tube and centrifuged (15 min at 12,000×g) at 4° C. Caproic acid, 0.1 mL, was added to 1 mL of the supernatant, which was then transferred into a Thundberg tube. The sample was frozen in liquid nitrogen, vacuum-sealed, and bathed overnight in liquid nitrogen. Subsequently, the sublimated sample was thawed for analysis by GC. The GC was equipped with a flame ionization detector and a polyethylene glycol packed column (1.5 m long, 5.6 mm ID). The column was operated at 100 to 150° C. with high purity helium, at 20 mL/min, as the carrier gas.

2.2—Results 2.2.1 Feed Consumption

Feed consumption was unaffected by inclusion of TTO in the diet at levels examined in Experiment 1 and this experiment (FIG. 5). Up to 7 days of age, feed consumption was highest on the L1 diet. Between hatch and 14 days, feed intake on the diet L1 and L2 was higher than on the negative or positive control diets. From hatch to 21 days, feed intake on the TTO-supplemented diets were between 4 and 5% lower than on the NC diet but similar to intake on the ZnB-supplemented diet. Over 35 days of feeding trial from hatch, feed intake was lowest on the L2 diet (by about 6% compared to NC) but intake on TTO-supplemented diets were comparable to the ZnB-supplemented diet. There were no significant differences between the groups.

2.2.2 Body Weight

At 35 days of age, birds raised on diet L1 were heavier than birds on the other treatment groups but this was not significantly different from the weight of the other groups, this group being on average 1.5 and 2.4% heavier than the NC and ZnB groups, respectively (FIG. 6). All other TTO groups and the ZnB group were lighter than the NC group. At 7 and 14 days, group H2 were the heaviest in weight while NC were heavier at 21 days than the treatment groups. These differences were not significant (P>0.05).

2.2.3 Feed Conversion Ratio

Group H2 were the most efficient in feed conversion between hatch and 7 as well as 14 days (FIG. 7). Between hatch and 21 days, however, birds on the L1 diet were 3% more efficient than those in the NC group while the H1 group were about 2% more efficient than the NC group at 35 days of age. These differences were not significant.

2.2.4 Weight of Visceral Organs

The relative weight of some of the visceral organs associated with digestion, absorption and immune function is shown in Table 4. The weight of the proventriculus+gizzard, small intestine and bursa at 7 days of age was slightly reduced (not significant) in birds on the TTO-supplemented diets, while the reverse was the case for the weight of the pancreas. The weight of the liver was increased (not significant) in chicks on diets supplemented with TTO up to 8 mg/kg. At 21 days of age, there was a reduction in the weight of the proventriculus+gizzard (P<0.05), small intestine and liver in chicks that were raised on TTO-supplemented diets. The weight of the pancreas was increased on diets containing TTO up to 8 mg/kg, while there was no definite trend in the weight of the bursa and spleen as a result of the dietary treatments.

TABLE 4

Relative weight (g/100 g body weight) of visceral organs at 7 and 21 days of age.

|  | NC | ZnB | L1 | L2 | M | H1 | H2 | SEM |
|---|---|---|---|---|---|---|---|---|
| Day 7 |  |  |  |  |  |  |  |  |
| Small intestine | 10.3 | 10.6 | 9.9 | 9.6 | 10.0 | 10.3 | 9.7 | 0.63 |
| Prov. + Gizz.[1] | 8.5 | 8.0 | 8.1 | 8.0 | 7.8 | 8.2 | 7.9 | 0.53 |
| Liver | 4.8 | 5.0 | 5.1 | 5.2 | 5.3 | 4.7 | 4.8 | 0.35 |
| Pancreas | 0.46 | 0.52 | 0.55 | 0.48 | 0.48 | 0.52 | 0.51 | 0.044 |
| Bursa | 0.17 | 0.16 | 0.15 | 0.15 | 0.16 | 0.16 | 0.14 | 0.017 |
| Day 21 |  |  |  |  |  |  |  |  |
| Small intestine | 6.4 | 6.4 | 6.5 | 6.0 | 6.3 | 6.5 | 5.8 | 0.40 |
| Pro + Gizz | 5.1[a] | 4.2[ab] | 4.9[ab] | 4.7[ab] | 4.3[ab] | 4.1[b] | 4.3[ab] | 0.35 |
| Liver | 3.1 | 3.3 | 3.0 | 3.1 | 3.1 | 2.9 | 2.8 | 0.23 |
| Pancreas | 0.31 | 0.27 | 0.35 | 0.32 | 0.33 | 0.30 | 0.28 | 0.031 |
| Bursa | 0.18 | 0.21 | 0.21 | 0.22 | 0.18 | 0.24 | 0.21 | 0.026 |
| Spleen | 0.08 | 0.09 | 0.09 | 0.11 | 0.08 | 0.09 | 0.08 | 0.013 |

SEM—Standard error of differences between mean values. Within the same age group, mean values in the same column not sharing a superscript are significantly different (P<0.05).

2.2.5 Mortality and Culls

A total of 5 birds were culled and 8 died, representing 3.87% mortality. Of this number, 3 (6.25% of the treatment group) each came from group NC, M and H1, and 2 (4.17%) each from ZnB and H2. One (2.08%) was culled from L2, and none died from L1. Details of the cause of death, including sex, are presented in Table 5.

TABLE 5

Distribution and causes of mortality/culls in Experiment 2

| Group | Cage No | Age at death (d) | Weight (g) | Sex | Comments |
|---|---|---|---|---|---|
| ZnB | 31 | 2 | 33 | M | Dehydration, culled |
| NC | 35 | 3 | 38.6 | M | Dehydration |
| NC | 22 | 4 | 58.6 | F | Runt, culled |
| M | 19 | 5 | 63.3 | F | Runt, dehydration |
| H2 | 42 | 7 | 58.9 | F | Runt, culled |
| L2 | 13 | 7 | 57 | M | Runt, culled |
| H2 | 30 | 8 | 69.8 | M | Starvation |
| NC | 1 | 8 | 151 | F | Peritonitis |
| H1 | 41 | 10 | 72 | F | Dehydration |
| ZnB | 31 | 2 | 246.5 | F | Dehydration |
| H1 | 32 | 14 | 97.3 | F | Typhilitis, culled |
| H1 | 28 | 15 | 396 | M | Ascites |
| M | 40 | 23 | 874.6 | M | Ascites |
| M | 6 | 28 | 414.9 | F | Peritonitis, culled |

2.2.6 Changes in Microbial Profiles

The microbial profiles of the ileum from birds on the different diets are shown in Table 6. At 21 days of age, the population of total anaerobes in the ileum was generally higher in chickens on diets supplemented with TTO than on the NC diet. The test supplement (TTO) also tended to increase the populations of lactic acid bacteria (LAB) and lactobacilli at this age but this effect was not significant. At 35 days of age, the reverse appeared to be the case, with birds on TTO-supplemented diets showing reduced (not significant) populations of LAB and lactobacilli. The populations of total anaerobes at 35 days, and C. perfringens and enterobacteria at both ages varied between replicates of the same treatment. The data for these species were therefore not subjected to statistical analysis.

TABLE 6

Populations of key microbial groups and species (Log CFU/g digesta) in the ileum and at 21 and 35 days of age.

| | Total anaerobes[1] | Lactic acid bacteria | Lactobacilli |
|---|---|---|---|
| 21 days | | | |
| NC | 5.7 | 7.0 | 6.3 |
| ZnB | 6.1 | 7.4 | 7.3 |
| L1 | 6.2 | 7.3 | 7.0 |
| L2 | 6.7 | 7.9 | 7.0 |
| M | 6.2 | 6.7 | 6.5 |
| H1 | 6.6 | 7.8 | 7.2 |
| H2 | 6.5 | 7.6 | 7.4 |
| SEM | 1.47 | 0.59 | 1.30 |
| 35 days | | | |
| NC | | 8.2 | 7.8 |
| ZnB | | 7.5 | 7.0 |
| L1 | | 7.5 | 7.7 |
| L2 | | 6.6 | 7.8 |
| M | | 7.1 | 6.5 |
| H1 | | 7.7 | 7.3 |
| H2 | | 5.9 | 7.3 |
| SEM | | 1.65 | 1.89 |

SEM—Standard error of differences between mean values.
[1]Data for 35 days were not analysed due to large within-treatment variability.

The populations of total anaerobes, LAB and enterobacteria in the caeca at 21 days of age were reduced (not significant) in chickens on the TTO-supplemented diets were lower than those in the NC group (Table 7). The populations of C. perfringens and lactobacilli were enumerated at this age but could not be statistically analysed as there were wide variations between replicates of some of the treatments. At 35 days of age, there were no effects of dietary treatment on the populations of LAB and lactobacilli. The populations of total anaerobes and enterobacteria were slightly increased in birds on the TTO-supplemented diets. The values for C. perfringens were not analysed due to strong within-treatment variability in some of the groups.

TABLE 7

Populations of key microbial groups and species (Log CFU/g digesta) in the caeca at 21 and 35 days of age.

| | Total anaerobes | Lactic acid bacteria | Enterobacteria | Lactobacilli[1] |
|---|---|---|---|---|
| 21 days | | | | |
| NC | 8.1 | 8.5 | 7.6 | |
| ZnB | 7.5 | 8.5 | 7.6 | |
| L1 | 6.8 | 8.6 | 7.7 | |
| L2 | 6.1 | 8.3 | 7.4 | |
| M | 7.7 | 8.4 | 7.4 | |
| H1 | 7.3 | 8.0 | 6.9 | |
| H2 | 6.8 | 8.1 | 7.3 | |
| SEM | 1.72 | 0.72 | 0.98 | |
| 35 days | | | | |
| NC | 8.3 | 8.8 | 6.0 | 8.3 |
| ZnB | 8.4 | 8.6 | 6.7 | 8.0 |
| L1 | 8.1 | 8.2 | 6.4 | 8.1 |
| L2 | 8.3 | 8.8 | 7.7 | 8.4 |
| M | 8.1 | 8.4 | 7.2 | 8.1 |
| H1 | 8.7 | 8.9 | 7.2 | 8.7 |
| H2 | 7.8 | 8.2 | 7.4 | 8.2 |
| SEM | 0.67 | 0.69 | 1.07 | 0.67 |

SEM—Standard error of differences between mean values.
[1]Data for 21 days were not analysed due to large within-treatment variability.

2.2.7 Concentrations of SCFAs

At 21 days of age, the concentration of acetic acid in the caecal digesta was significantly higher (P<0.001) in birds on the L2 diet than in chicks raised on other diets (Table 8). The concentration of acetic acid was also higher in the L1 chicks than the NC chicks but this was not significant. The concentration of propionic acid in birds on the TTO-supplemented diets also tended to be higher (not significant) than that of birds on the NC diet. Butyric+isobutyric acids (P<0.01) and valeric+isovaleric acids (P<0.05) were generally higher in birds on the diets supplemented with TTO than those raised on the NC diet. At 35 days of age, the concentration of propionic acid was lower (P<0.05) in birds raised on the ZnB-supplemented diet than on the other diets. There was also less isobutyric+butyric acids in the L1 chicks than in the other chicks but this was significant (P<0.05) only when compared to the L2 and M groups. The concentrations of these SCFAs were also measured in the ileal digesta but the data were not statistically analysed due to large within-treatment variability in some of the groups.

TABLE 8

Concentrations of SCFAs (µmol/g digesta) in the caeca at 21 and 35 days of age.

| | Acetic acid | Propionic acid | Isobutyric + Butyric acids | Isovaleric + valeric acids |
|---|---|---|---|---|
| 21 days | | | | |
| NC | 38.1$^{bc}$ | 1.78 | 10.2$^a$ | 0.44$^b$ |
| ZnB | 47.9$^b$ | 2.64 | 12.3$^a$ | 0.80$^{ab}$ |
| L1 | 48.9$^b$ | 2.24 | 11.3$^a$ | 0.60$^{ab}$ |
| L2 | 66.8$^a$ | 2.89 | 11.6$^a$ | 0.98$^a$ |

TABLE 8-continued

Concentrations of SCFAs (μmol/g digesta) in the caeca at 21 and 35 days of age.

| | Acetic acid | Propionic acid | Isobutyric + Butyric acids | Isovaleric + valeric acids |
|---|---|---|---|---|
| M | 33.5$^{bc}$ | 1.55 | 6.2$^b$ | 0.50$^b$ |
| H1 | 49.4$^b$ | 2.52 | 13.7$^a$ | 0.83$^{ab}$ |
| H2 | 30.8$^c$ | 2.13 | 10.3$^{ab}$ | 0.71$^{ab}$ |
| SEM 35 days | 10.79*** | 1.111 | 2.81** | 0.310* |
| NC | 46.7 | 4.34$^a$ | 10.1$^{ab}$ | 0.91 |
| ZnB | 39.4 | 2.64$^b$ | 10.7$^{ab}$ | 0.67 |
| L1 | 46.8 | 4.23$^{ab}$ | 4.8$^b$ | 0.75 |
| L2 | 59.7 | 5.99$^a$ | 12.4$^a$ | 1.00 |
| M | 47.6 | 5.72$^a$ | 12.0$^a$ | 0.83 |
| H1 | 48.7 | 3.72$^{ab}$ | 8.7$^{ab}$ | 0.75 |
| H2 | 52.7 | 4.42$^{ab}$ | 9.0$^{ab}$ | 0.71 |
| SEM | 16.12 | 1.889* | 3.61* | 0.282 |

SEM—Standard error of differences between mean values.
Within the same age group, mean values in the same column not sharing a superscript are significantly different (*P < 0.05; P < 0.01; *P < 0.001).

Figure 8A:
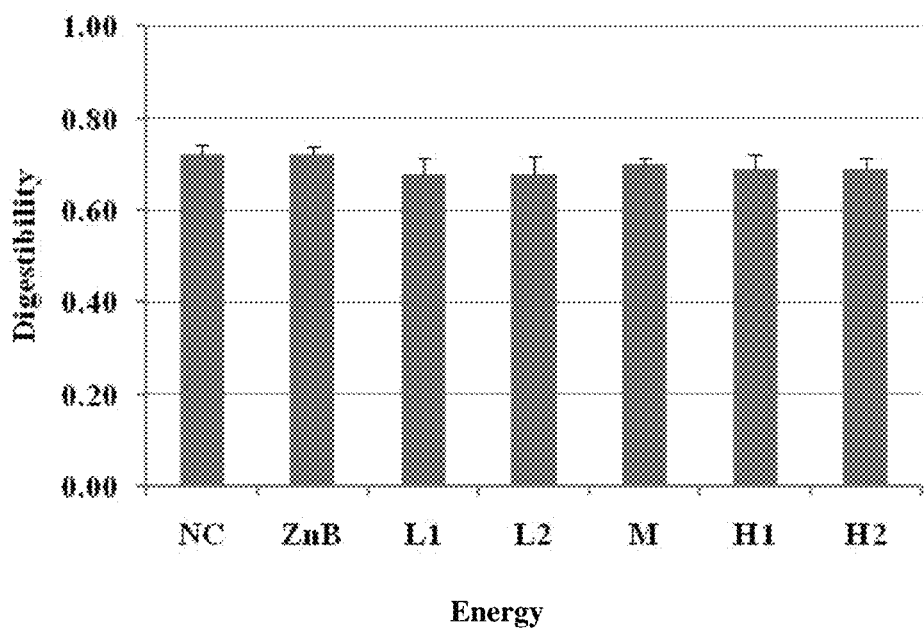
FIGS. 8A, 8B and 8C: Ileal digestibility of starch, protein and energy at 21 days of age.
Figure 8B:
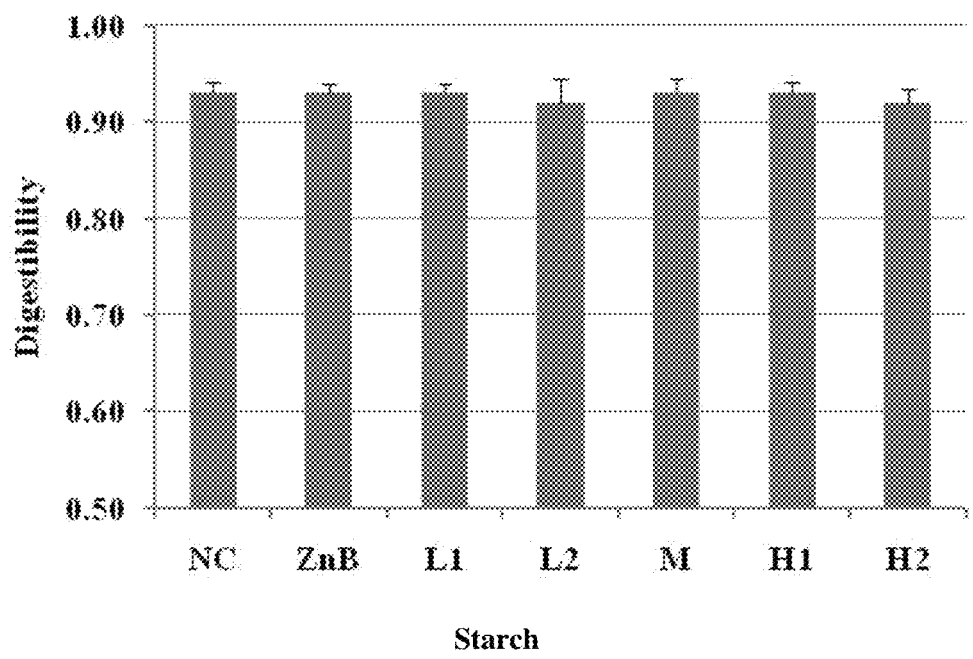
Figure 8C:
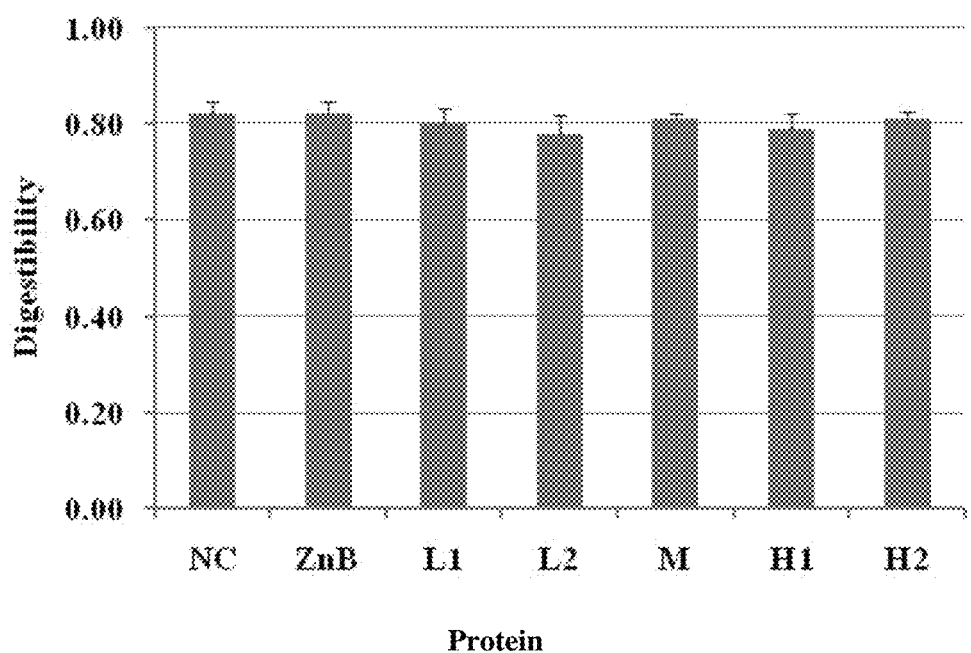
Figure 9A:
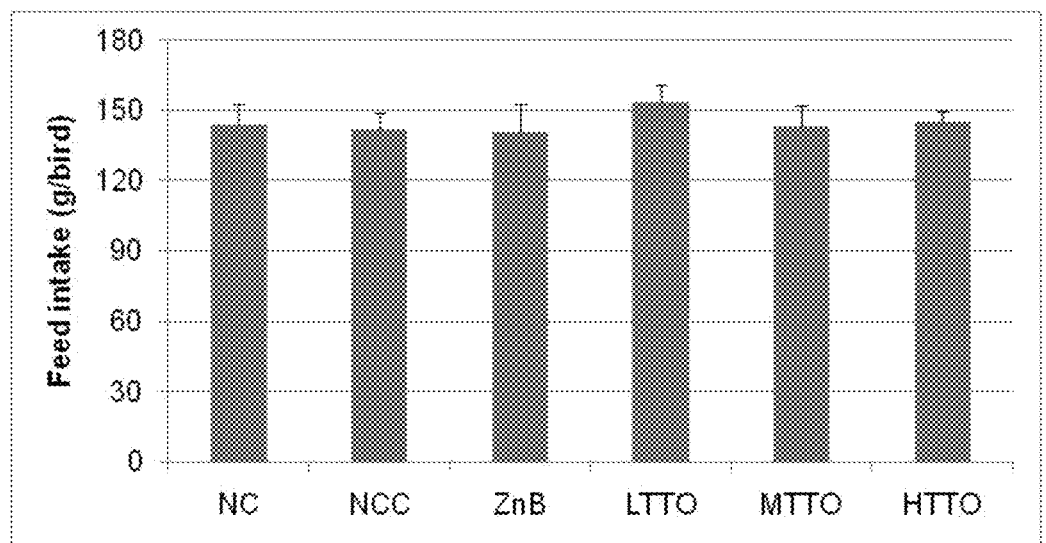
FIGS. 9A, 9B, 9C and 9D: Feed intake (g/bird) over different periods of growth on different treatments.
Figure 9B:
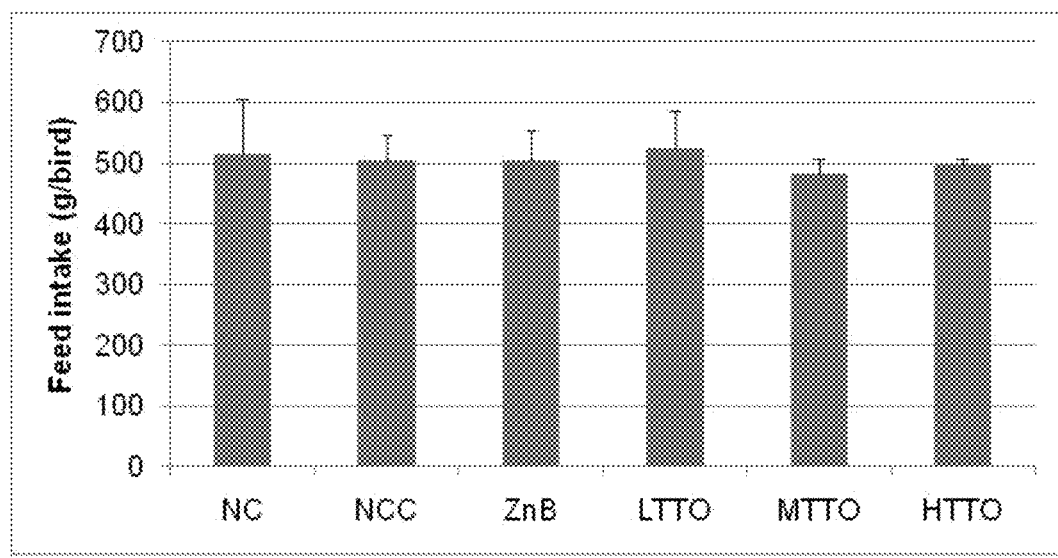
Figure 9C:
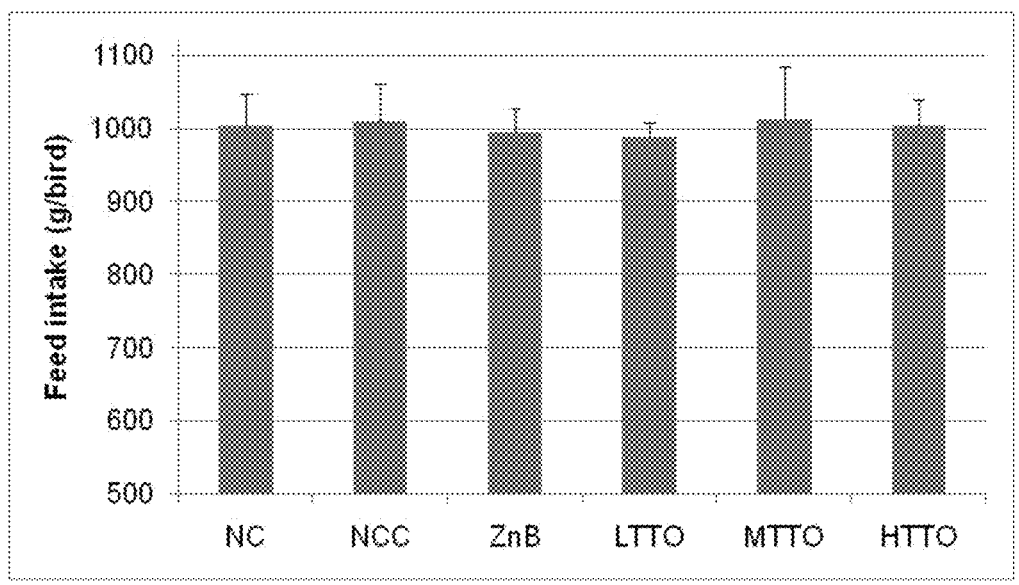
Figure 9D:
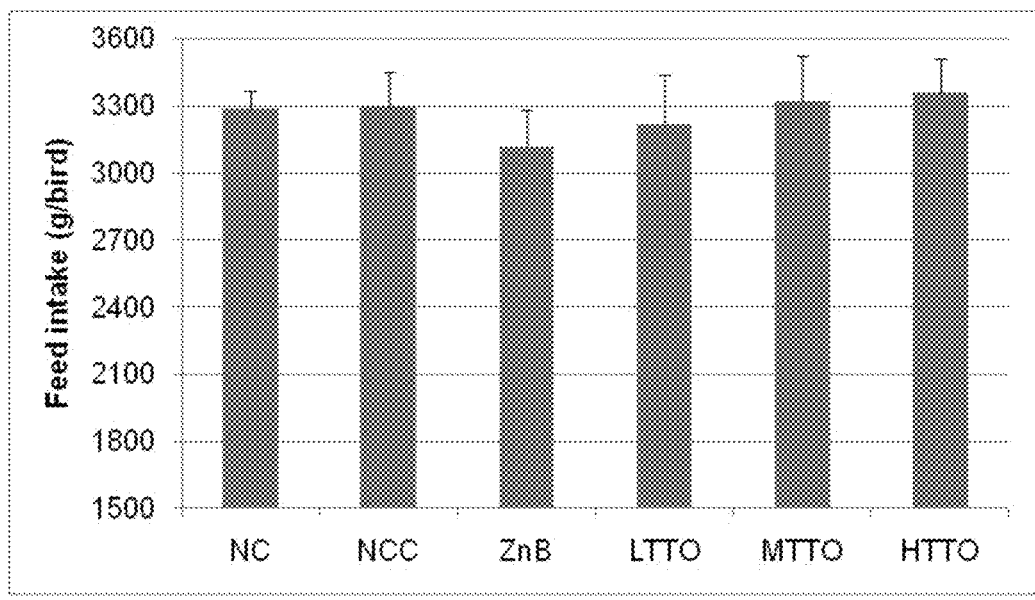
Figure 10A:
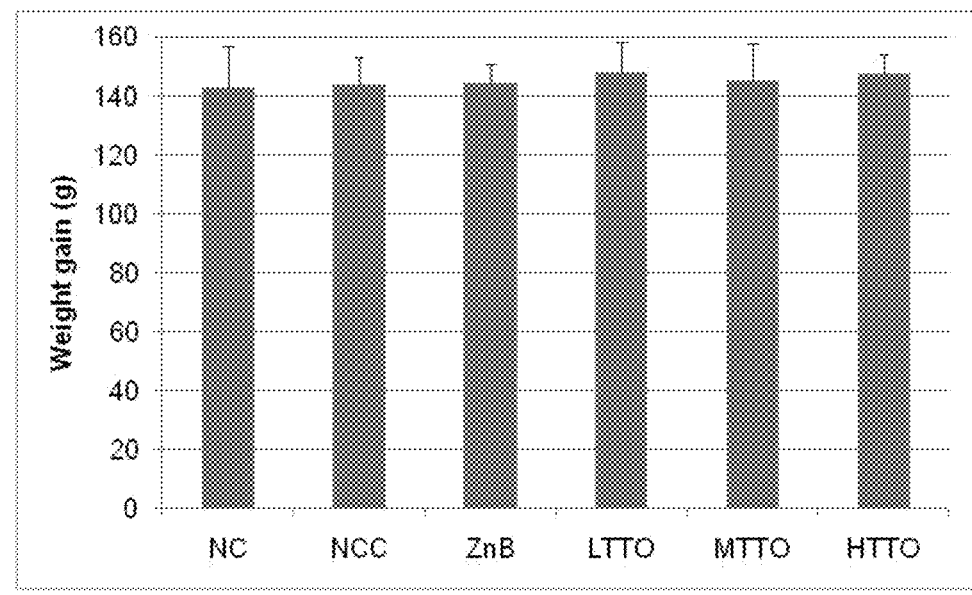
FIGS. 10A, 10B, 10C and 10D: Body weight of birds (g) at different ages on different treatments.
Figure 10B:
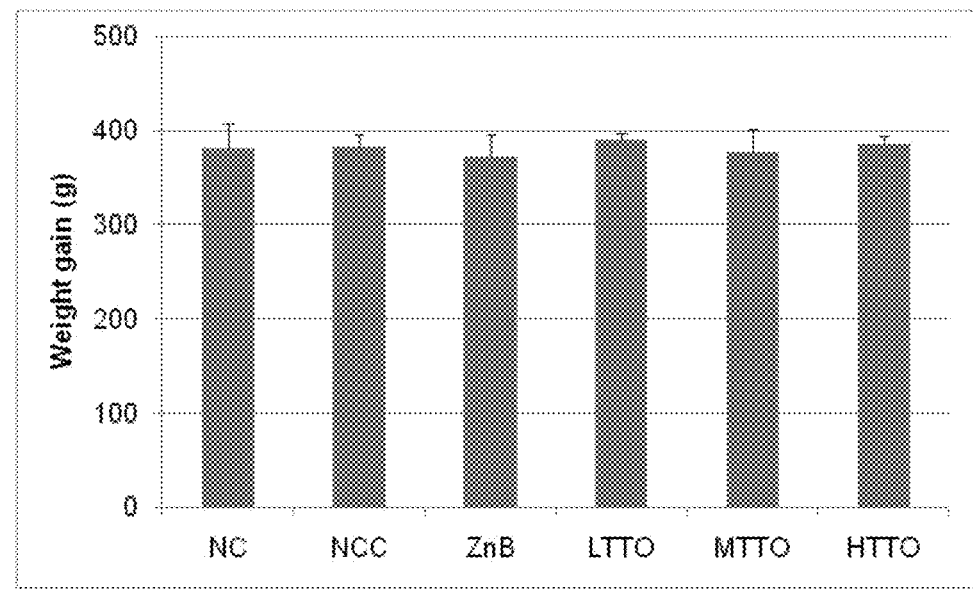
Figure 10C:
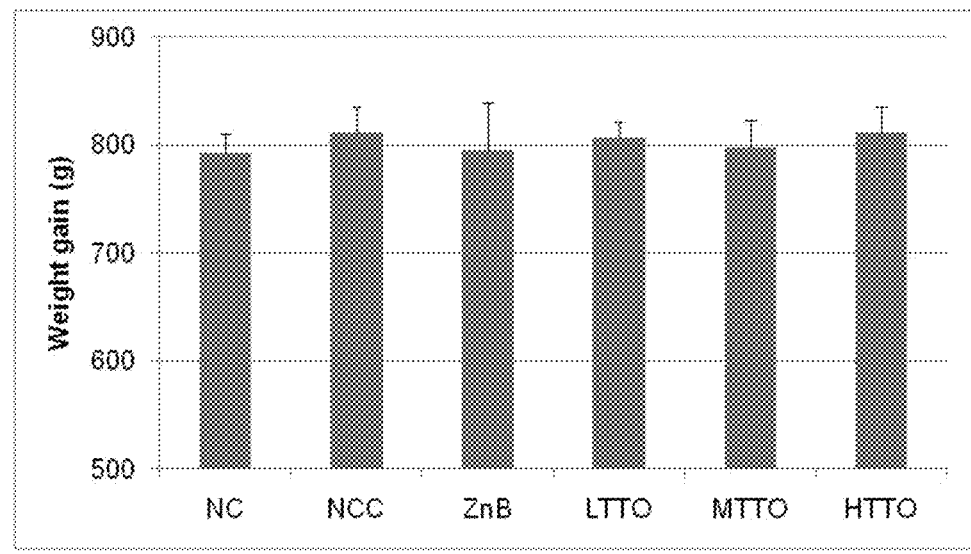
Figure 10D:
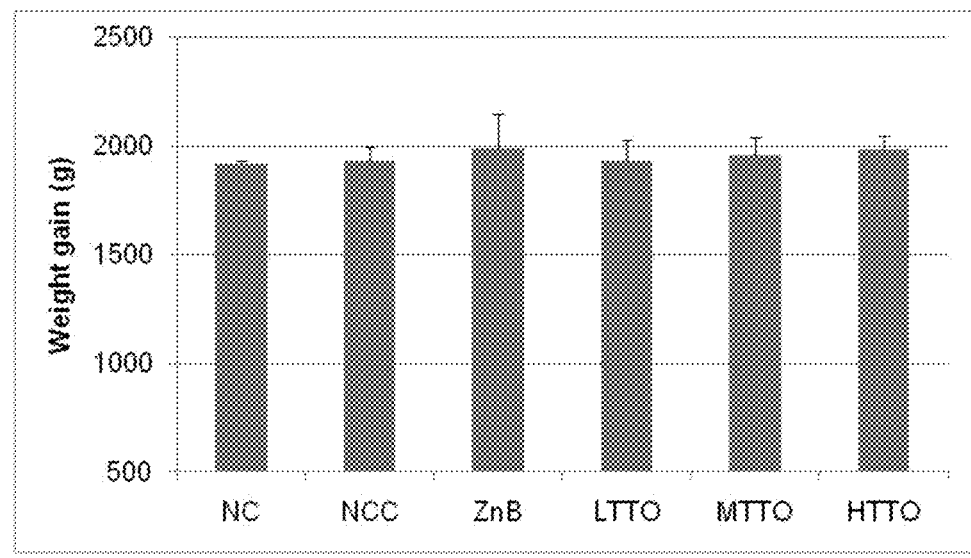
Figure 11A:
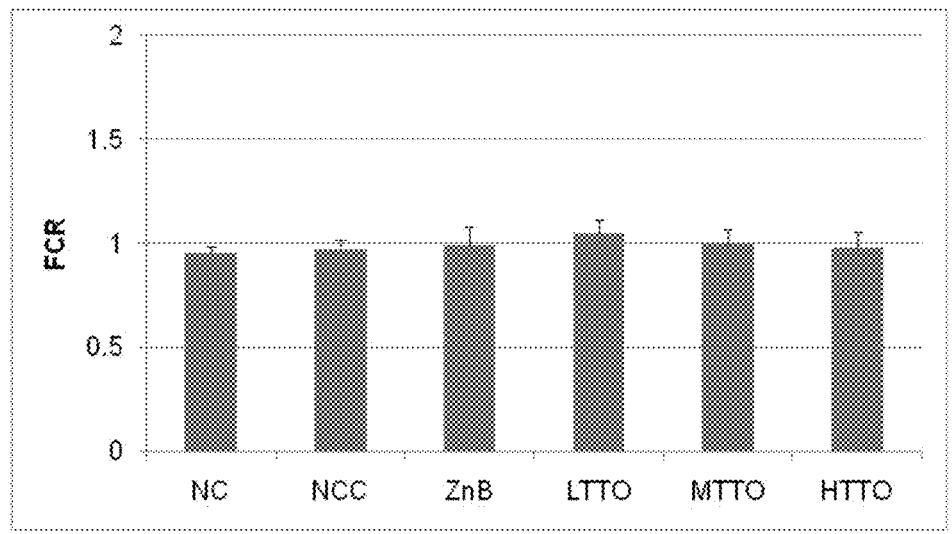
FIGS. 11A, 11B, 11C and 11D: Feed conversion ratio (g feed/g weight gain) over different periods of growth on different treatments.
Figure 11B:
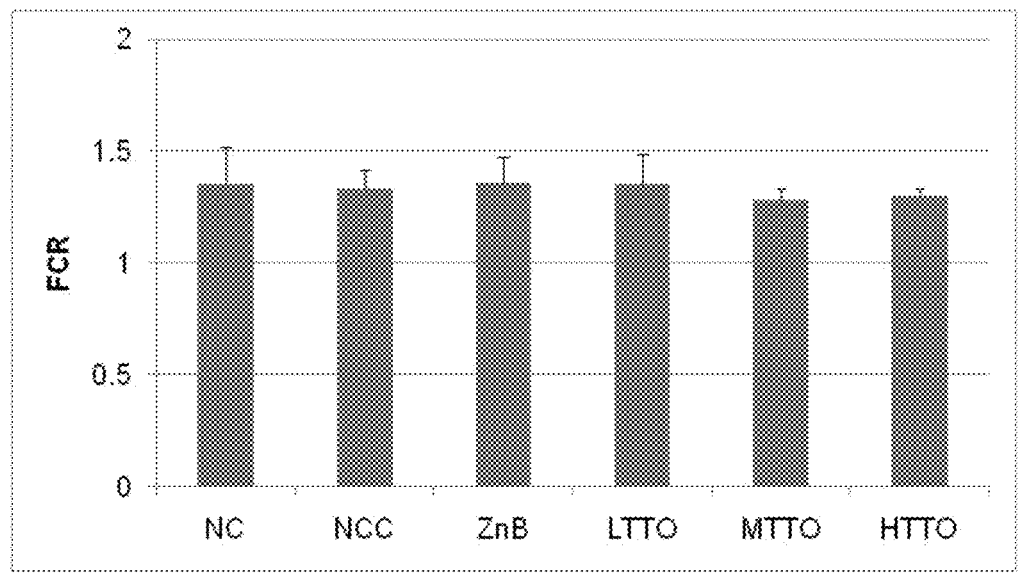
Figure 11C:
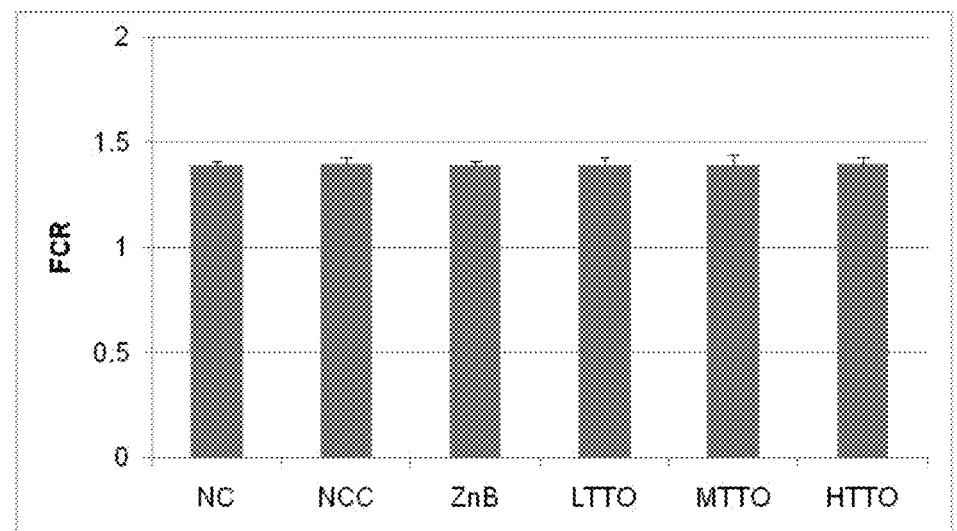
Figure 11D:
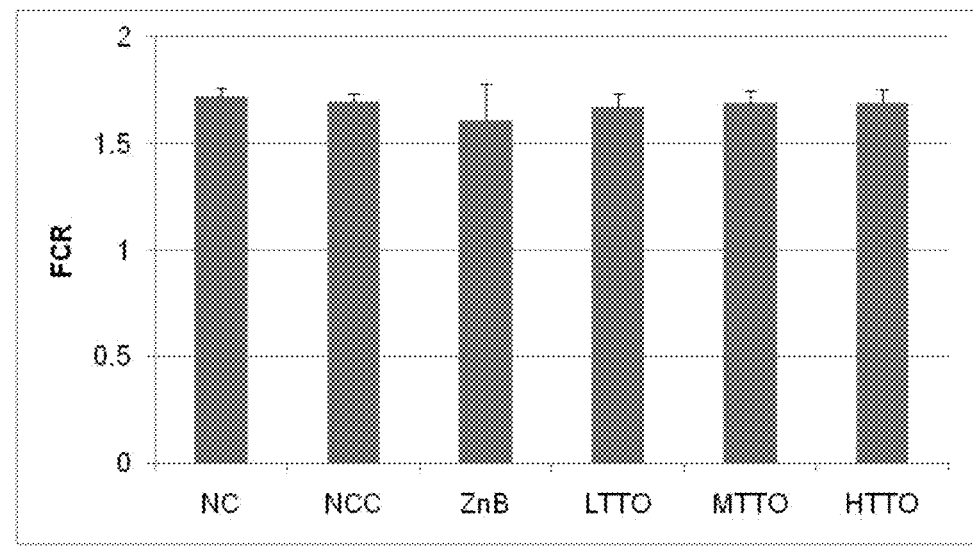

At 21 days of age, the ileal digestibility of starch and protein were comparable between the groups (FIG. 8). However, energy digestibility was lowest in chicks from the L1 and L2 group but this differed significantly (P<0.05) only from the ZnB group.

Example 3—Testing the Prophylactic Potential of Tea Tree Oil Against Development of Necrotic Enteritis in Broiler Chickens 3.1—Experimental Protocol
3.1.1 Birds and Management This experiment was of semi-commercial scale, designed to test response to disease (*Salmonella sofia*) challenge. Nine hundred mixed-sex chicks (initial weight, 47.7±1.06 g) were involved and these were randomly divided into six groups; a negative unchallenged group (NC), negative challenged (NCC), Zn-bacitracin challenged (ZnB), low TTO challenged (LTTO), mid TTO challenged (MTTO) and high TTO challenged (HTTO). The corresponding amounts of TTO used for LTTO, MTTO and HTTO, respectively were 2, 8 and 16 mg/kg diet during the starter phase (1-21 days), and 3, 12 and 24 mg/kg diet in the finisher phase. Each of the 6 treatments was allocated to 6 single pen replicates, each containing 25 (13 male and 12 female) birds at 1 day of age. All pen group weights were within 6% of the mean pen group weight.

Birds and feeds were weighed weekly from 1 day of age to measure growth rate, feed consumption and feed conversion efficiency (ratio). Birds were monitored for the usual signs of infection with this agent, which include drowsiness, huddling in corners, watery yellowish diarrhoea, and rarely death. Mortality was assessed as it occurred and full post-mortem examination conducted by a State registered Vet. Three birds (2 males and 1 female) were randomly selected and slaughtered on days 21 and 35 for assessment of digesta pH, microbial profiles and concentrations of SCFAs, as described for Experiment 2. The randomization of replicates by groups is presented in Table 9.

TABLE 9

Randomization of replicates in Experiment 3

| Treatment Group | Code | Dose Starter (0-21 d) | Dose Finisher (21-35 d) | Replicate No. |
|---|---|---|---|---|
| Negative Control (vehicle, no challenge) | NC | 0 | 0 | 1, 2, 18, 19, 35, 36 |
| Negative Control (vehicle, challenged) | NCC | 0 | 0 | 4, 9, 14, 21, 24, 32 |
| Positive Control (Zn Bacitracin, ppm) | ZnB | 50 | 50 | 3, 8, 10, 15, 23, 29 |
| TTO (mg/kg diet) | LTTO | 2 | 3 | 7, 11, 16, 20, 27, 34 |
| | MTTO | 4 | 6 | 6, 12, 17, 26, 30, 33 |
| | HTTO | 8 | 12 | 5, 13, 20, 25, 28, 31 |

3.1.2 *Salmonella* Challenge Protocol

Two days prior to inoculation with the disease agent, *Salmonella sofia* was cultured in Brain Heart Infusion broth (Oxoid, Hampshire, UK), over 24 hours at 39° C. The resulting culture was then centrifuged at 5000×g for 15 minutes at 21° C. The supernatant was poured off and the residual pellet resuspended in sterile PBS (phosphate buffered saline solution, pH 7-7.5). The final concentration of *S. sofia* in PBS ranged from 1.2 to 3.1×10$^9$ CFU/mL.

At 3, 8 and 13 days of age, each of the challenged birds (treatments 2 through 6) received 1 mL, 2 mL and 2 mL, respectively, of the *S. Sofia*/PBS solution via oral gavage. Unchallenged birds (treatment 1) received sterile PBS in place of the *Salmonella* solution in accordance with the protocol used for challenged birds.

3.2—Results
3.2.1 Feed Consumption

Results of feed intake, assessed weekly from hatch to 35 days, are shown in FIG. 9. There were no significant differences between the groups at any stage in the investigation. Up to 7 days of age, group LTTO ate about 6 and 8% more feed than the negative unchallenged and ZnB-challenged groups, respectively. During the starter phase (1-21 days) there were only marginal differences between the groups in feed consumption. Over 35 days of feeding, feed consumption on the ZnB diet was 5.5% lower than on the negative unchallenged group. Feed consumption on the LTTO diet was also 2% less than on the negative unchallenged group but increased by 1 and 2%, respectively on the MTTO and HTTO diets. Compared to the negative challenged group, feed intake on the LTTO (all challenged) groups were reduced (except MTTO) up to 21 days of age. Over 35 days, feed intake was reduced (2.3%) on LTTO but increased on the MTTO (about 1%) and HTTO (2%) diets.

3.2.2 Body Weight

At 7 days, live weight was highest (not significant) on the LTTO diet (FIG. 10). The supplement, TTO, increased the weight at 21 days by between 0.6 and 2.4%, compared to the negative unchallenged diet, and between 0.3 and 2% when compared to the ZnB group. At 35 days of age, group HTTO was 3.5% heavier than the negative unchallenged group. At 21 days of age, the LTTO and MTTO groups were slightly lighter (less than 1%) than the negative challenged group but group HTTO were heavier (less than 1%). Groups MTTO and HTTO were 1 and 2.5%, respectively heavier than the negative challenged group while LTTO was lighter (less than 1%). None of these differences was significant.

3.2.3 Feed Conversion Ratio

Birds on the negative challenge and HTTO diets were less efficient (less than 1%) than birds on the negative control diet, while FCR to 21 days was similar in birds on the other diets (FIG. 11). Compared to the negative challenged group, birds on ZnB, LTTO and MTTO were more efficient (less than 1%) in feed conversion, while group HTTO had the same FCR as the negative challenge group. Between hatch and 35 days, FCR was between 1.8 and 3% better on the TTO-supplemented diets than on the negative control diet. The TTO groups were less efficient (up to 4.7%) than the ZnB group but more efficient (up to 1.8%) than the negative challenged group.

3.2.4 Symptoms of Infectivity

All groups responded as expected to inoculation of disease agent at 3 days of age. Typical symptoms of the disease challenge were observed, notably huddling in corners of the cage, somnolence and loss of appetite (data not shown). Birds were generally depressed and reluctant to move. These symptoms were transient, being pronounced for about 8 hours, then disappearing gradually to a full recovery within 24 hours. Some of the chicks developed a pasty vent, following some diarrhoea. The repeat challenges on days 8 and 13 did not produce these symptoms as dramatically as during the first challenge.

3.2.5 Mortality and Culls

Mortality was relatively low, at only about 1.6%; about half of these being culls, when it was determined that the chicks would not survive. All but one of the deaths happened in the first week, possibly in response to the first inoculation. In terms of distribution by treatment groups, mortality was 1.3, 2.0, 0.0, 0.7, 2.0 and 0.7%, respectively in the NC, NCC, LTTO, MTTO, HTTO and ZnB groups. Most of the birds that were culled were dehydrated, indicating inability to eat or drink following the challenge with the disease agent. Other causes of death and reasons for culling are listed in Table 10.

TABLE 10

Distribution and causes of mortality/culls in Experiment 3.

| Cage | Group | Sex | Age at death (d) | Weight (g) | Comments |
|---|---|---|---|---|---|
| 28 | HTTO | M | 1 | 47 | Omphalitis |
| 5 | HTTO | M | 4 | 54 | Peritonitis, omphalitis |
| 36 | NC | F | 4 | 30 | Culled, Dehydrated |
| 3 | ZNB | F | 4 | 37 | Dehydration |
| 15 | ZNB | M | 4 | 39 | Not determined |
| 33 | MTTO | M | 5 | 37 | Culled, Dehydrated |
| 14 | NCC | F | 5 | 39 | Culled, Dehydrated |
| 36 | NC | M | 5 | 36 | Culled, Dehydrated |
| 9 | NCC | M | 6 | 86 | Suspect typhylitis |
| 8 | ZNB | F | 6 | 59 | Culled, pasty vent |
| 29 | ZNB | M | 6 | 88 | Ascites and heart failure |
| 4 | NCC | M | 7 | 38 | Culled, Dehydrated |
| 23 | ZNB | F | 7 | 32 | Culled, Dehydrated |
| 28 | HTTO | F | 8 | 132 | Not determined |

3.2.6 Microbial Profiles

The populations of key microbial species and groups in the ileum are shown in Table 11. There were no significant differences between the populations of coliforms, TAB and lactobacilli at 21 days of age. However, TTO significantly increased (P<0.05) the population of LAB in the ileum, when compared to the NC group. The data for *C. perfringens* at this age were not analysed due to within-treatment variability of some of the groups. At 35 days of age, the population of coliforms on the ZnB-supplemented diet was lower (P<0.05) than that of the NC group but was generally similar to the TTO-supplemented groups. The test agent, TTO, at the lowest and highest levels of inclusion also resulted in a higher (P<0.01) population of lactobacilli, when compared to the NC group. The populations of LAB, TAB and *C. perfringens* were slightly higher in the groups supplemented with TTO.

TABLE 11

Populations of key microbial groups and species (Log CFU/g digesta) in the ileum at 21 and 35 days of age.

|  | Coliforms | LAB | TAB[1] | *C. perfringens*[1] | Lactobacilli |
|---|---|---|---|---|---|
| 21 days |  |  |  |  |  |
| NC | 4.0 | 6.8$^b$ | 7.0 |  | 6.2 |
| NCC | 4.9 | 7.2$^{ab}$ | 7.1 |  | 6.1 |
| ZnB | 4.4 | 7.3$^{ab}$ | 7.3 |  | 6.6 |
| LTTO | 5.1 | 7.7$^a$ | 7.4 |  | 6.7 |
| MTTO | 4.5 | 7.4$^{ab}$ | 7.3 |  | 6.3 |
| HTTO | 4.8 | 7.3$^{ab}$ | 7.3 |  | 6.2 |
| SEM | 0.82 | 0.22* | 0.23 |  | 0.43 |
| 35 days |  |  |  |  |  |
| NC | 4.4$^a$ | 7.2 | 7.0 | 3.0 | 6.0$^b$ |
| NCC | 3.0$^{ab}$ | 7.4 | 7.4 | 2.9 | 6.6$^{ab}$ |
| ZnB | 2.8$^b$ | 7.3 | 7.5 | 3.3 | 6.7$^{ab}$ |
| LTTO | 3.4$^{ab}$ | 7.8 | 8.0 | 2.9 | 7.7$^a$ |
| MTTO | 3.1$^{ab}$ | 7.6 | 7.6 | 2.8 | 7.3$^{ab}$ |
| HTTO | 3.7$^{ab}$ | 7.8 | 7.9 | 3.5 | 7.6$^a$ |
| SEM | 0.82* | 0.30 | 0.34 | 1.07 | 0.46** |

SEM—Standard error of differences between mean values.
Within the same age group, mean values in the same column not sharing a superscript are significantly different (*P < 0.05; **P < 0.01).
[1]*C. perfringens* was assessed at both ages but data for 21 days were not analysed due to wide intra-group variability.

At 21 days of age, the population of coliforms and LAB in the caeca of birds on the TTO- and ZnB-supplemented diets were generally higher (not significant) than that of the NC group (Table 12). There were no changes in the populations of TAB, lactobacilli and *C. perfringens* as a result of dietary treatment. The population of coliforms and lactobacilli in the caeca at 35 days of age was increased (P<0.01) as a result of supplementation with TTO and to a lesser extent, ZnB There was no definite trend in the effect of the test supplement, TTO, on the population of *C. perfringens*.

TABLE 12

Populations of key microbial groups and species (Log CFU/g digesta) in the caeca at 21 and 35 days of age.

|  | Coliforms | Lactic acid bacteria | TAB | Lactobacilli | *C. perfringens* |
|---|---|---|---|---|---|
| 21 Days |  |  |  |  |  |
| NC | 6.9 | 8.0 | 8.5 | 7.8 | 5.6 |
| NCC | 7.0 | 8.4 | 8.5 | 8.0 | 4.9 |
| ZnB | 7.0 | 8.4 | 8.5 | 8.0 | 4.9 |
| LTTO | 7.2 | 8.7 | 8.6 | 7.9 | 5.6 |
| MTTO | 6.8 | 8.4 | 8.4 | 7.7 | 5.2 |
| HTTO | 7.2 | 8.4 | 8.5 | 7.6 | 5.8 |
| SEM | 0.17 | 0.28 | 0.26 | 1.02 | 0.97 |
| 35 days |  |  |  |  |  |
| NC | 6.2$^b$ | 8.6 | 8.6 | 7.9$^b$ | 3.0 |
| NCC | 6.3$^b$ | 8.5 | 8.6 | 7.9$^b$ | 2.9 |
| ZnB | 7.0$^a$ | 8.7 | 8.8 | 8.2$^b$ | 3.3 |
| LTTO | 6.9$^a$ | 8.8 | 9.0 | 8.8$^a$ | 2.9 |
| MTTO | 6.6$^{ab}$ | 8.7 | 8.8 | 8.3$^{ab}$ | 2.8 |

TABLE 12-continued

Populations of key microbial groups and species (Log CFU/g digesta) in the caeca at 21 and 35 days of age.

|  | Coliforms | Lactic acid bacteria | TAB | Lactobacilli | *C. perfringens* |
|---|---|---|---|---|---|
| HTTO | 6.9$^a$ | 8.9 | 9.0 | 8.5$^a$ | 3.5 |
| SEM | 0.23** | 0.23 | 0.15 | 0.21** | 1.07 |

SEM—Standard error of differences between mean values.
Within the same age group, mean values in the same column not sharing a superscript are significantly different (**P < 0.01).

3.2.7 Concentrations of Short-Chain Fatty Acids in the Small Intestine and Caeca At 21 days of age, the concentrations of acetic (P<0.05) and isobutyric+butyric (P<0.001) acids were higher in chicks on the TTO-supplemented diets than on the control diets (Table 13). The concentration of succinic acid was highest (P<0.001) in chicks on the negative challenged group and similar in the other five groups tested. No differences were found between the groups in the concentrations of propionic and isovaleric+valeric acids. At 35 days of age, the concentrations of acetic, propionic and isobutyric+butyric acids were generally higher in the TTO-supplemented groups but this did not differ significantly from the control groups. The concentrations of these SCFAs were low in the ileum at both periods assessed, and were too variable within the groups to be statistically tested.

TABLE 13

Concentrations of SCFAs (μmol/g digesta) in the caeca at 21 and 35 days of age.

|  | Acetic acid | Propionic acid | Isobutyric + Butyric acids | Isovaleric + valeric acids | Succinic acid |
|---|---|---|---|---|---|
| 21 days |  |  |  |  |  |
| NC | 52.5$^b$ | 2.9 | 7.7$^b$ | 0.79 | 3.5$^b$ |
| NCC | 56.4$^b$ | 3.3 | 6.5$^b$ | 0.69 | 8.5$^a$ |
| ZnB | 62.5$^{ab}$ | 3.2 | 13.2$^a$ | 0.84 | 5.1$^b$ |
| LTTO | 60.5$^b$ | 3.0 | 11.5$^a$ | 0.98 | 4.0$^b$ |
| MTTO | 86.1$^a$ | 4.0 | 15.2$^a$ | 0.80 | 3.1$^b$ |
| HTTO | 62.6$^{ab}$ | 3.1 | 10.5$^{ab}$ | 0.82 | 4.0$^b$ |
| SEM | 15.26* | 1.20 | 3.11*** | 0.135 | 1.90*** |
| 35 days |  |  |  |  |  |
| NC | 52.8 | 4.8 | 9.5 | 1.08 | 3.4 |
| NCC | 68.0 | 5.7 | 11.4 | 1.12 | 4.0 |
| ZnB | 68.7 | 6.4 | 14.1 | 1.26 | 3.2 |
| LTTO | 60.2 | 7.3 | 12.8 | 1.31 | 2.9 |
| MTTO | 77.6 | 6.9 | 16.7 | 1.50 | 3.3 |
| HTTO | 69.5 | 7.8 | 12.9 | 1.23 | 5.1 |
| SEM | 14.34 | 1.13 | 3.95 | 0.243 | 1.83 |

SEM—Standard error of differences between mean values.
Within the same age group, mean values in the same column not sharing a superscript are significantly different (*P < 0.05; ***P < 0.001).

From the results obtained in this study, the test supplement did not negatively affect feed consumption, body weight or FCR. The tea tree oil did produce some effects on gut microbial profiles that were different from those of the negative control and often similar to the positive control. In addition, the test agent was superior to zinc bacitracin in body weight of chicks at 35 days. Tea tree oil at the lowest test level improved 35-day weight by 6, 1.5 and 0.74% in experiments 1, 2 and 3, respectively. The corresponding values for zinc bacitracin were 5, −1 and 0.06%. Protection against disease, rather than improvement in productivity per se is the main reason that antibiotics are used in the poultry industry. Antibiotic supplements rarely improve productivity beyond 3-5%, depending on the disease status of the environment. In the present study, tea tree oil supported growth following challenge with *S. sofia* comparably to, and often better than zinc bacitracin. In addition, the impact of tea tree oil was noticeable from around 2 mg/kg diet, making it suitable for application at these low levels. No negative effects on digestive function or health of chicks were observed, and tea tree oil also supported productivity as well as zinc bacitracin under disease challenge. Furthermore, the tea tree oil left no residue in meat or manure when used at low levels, suggesting that its use will not reduce meat quality or constitute an environmental hazard. All of these results support the application of tea tree oil as a replacement for antibiotic supplements.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

What is claimed is:

1. A composition consisting essentially of tea tree oil encapsulated by cyclodextrin and an oil selected from the group consisting of rapeseed oil and canola oil;
   wherein the tea tree oil is present in an amount sufficient to reduce a bacterial infection in an animal upon ingestion of the composition, and wherein the tea tree oil is at an amount of between 2 milligrams per kilogram and 70 milligrams per kilogram of the composition.

2. The composition of claim 1, wherein the canola oil is present in an amount of 20 milliliters per kilogram of the composition.

3. The feed composition of claim 1, further consisting essentially of a component selected from the group consisting of wheat, sorghum, mung beans, tallow, canola meal, cottonseed meal, soybean meal, zinc bacitracin and combinations thereof.

4. The feed composition of claim 1, wherein ingestion of the composition maintains levels of feed consumption, body weight, efficiency of feed utilization, and gut microbial profile of the animal.

5. A method of treating an animal with a bacterial infection consisting essentially of feeding the animal the composition of claim 1.

6. The method of claim 5, wherein tea tree oil is present at an amount of between 2 milligrams per kilogram and 32 milligrams per kilogram of the composition.

7. The method of claim 5, wherein tea tree oil is present at an amount of between 3 milligrams per kilogram and 48 milligrams per kilogram of the composition.

8. A method of preparing the composition of claim 1, consisting essentially of:
   (a) encapsulating tea tree oil in cyclodextrin;
   (b) combining the tea tree oil encapsulated in cyclodextrin and an oil selected from the group consisting of rapeseed oil and canola oil to form the composition of claim 1.

9. The method of claim 8, wherein the canola oil is present in an amount of 20 milliliters per kilogram of the composition.

10. The method of claim 9, wherein step (a) is performed at least 12 hours or at least 24 hours prior to step (b).

* * * * *